United States Patent

Haff et al.

[11] Patent Number: 5,885,775
[45] Date of Patent: Mar. 23, 1999

[54] METHODS FOR DETERMINING SEQUENCES INFORMATION IN POLYNUCLEOTIDES USING MASS SPECTROMETRY

[75] Inventors: Lawrence A. Haff, Wilton, Conn.; Igor Pavlovich Smirnov, Brookline, Mass.

[73] Assignee: PerSeptive Biosystems, Inc., Framingham, Mass.

[21] Appl. No.: 726,090

[22] Filed: Oct. 4, 1996

[51] Int. Cl.[6] .............................. C12Q 1/68; C12P 19/34; G01N 24/00

[52] U.S. Cl. ........................... 435/6; 435/91.2; 435/91.5; 436/173; 935/8; 935/17; 935/77; 935/78

[58] Field of Search ....................... 536/24.33; 436/173; 435/6, 91.2, 91.5, 91.1; 935/8, 17, 77, 78

[56] References Cited

U.S. PATENT DOCUMENTS

| | | | |
|---|---|---|---|
| 4,865,968 | 9/1989 | Orgel et al. | 435/6 |
| 4,942,124 | 7/1990 | Church | 435/6 |
| 5,045,694 | 9/1991 | Beavis et al. | 250/287 |
| 5,104,791 | 4/1992 | Abbott et al. | 435/6 |
| 5,288,644 | 2/1994 | Beavis et al. | 436/94 |
| 5,453,247 | 9/1995 | Beavis et al. | 422/68.1 |
| 5,547,835 | 8/1996 | Köster | 435/6 |
| 5,605,798 | 2/1997 | Köster | 435/6 |
| 5,614,365 | 3/1997 | Tabor et al. | 435/6 |
| 5,622,824 | 4/1997 | Köster | 435/6 |

FOREIGN PATENT DOCUMENTS

| | | |
|---|---|---|
| WO 94/16101 | 7/1994 | WIPO . |
| WO 95/14108 | 5/1995 | WIPO . |
| WO 96/30545 | 3/1996 | WIPO . |
| WO 96/29431 | 9/1996 | WIPO . |
| WO 96/37630 | 11/1996 | WIPO . |
| WO 96/27681 | 12/1996 | WIPO . |
| WO97/35033 | 9/1997 | WIPO . |
| WO97/41258 | 11/1997 | WIPO . |

OTHER PUBLICATIONS

Tang et al. Rapid Communications in Mass Sepectrometry 7:63–66 (1993).
Cotton. Mutation Research 285:125–144 (Jan. 1993).
Jones et al eds. RNA Isolation & Analysis. Bios Scientific Publishers (1994) pp. 109–111, & 133–139.

(List continued on next page.)

Primary Examiner—W. Gary Jones
Assistant Examiner—Debra Shoemaker
Attorney, Agent, or Firm—Testa, Hurwitz & Thibeault, LLP

[57] ABSTRACT

The invention relates to methods for determining sequence information in polynucleotides by combining the recent disparate technologies of mass spectrometry and polynucleotide hybridization, amplification, extension and/or ligation techniques. Broadly, in a first step, the method for determining sequence information in a sample polynucleotide includes hybridizing with a sample nucleotide one or a mixture of oligonucleotide probes having a nucleotide sequence complementary to a portion of the sample polynucleotide, thereby forming a complex. Then, in a second step, the complex is contacted with at least a member selected from the group consisting of nucleosides, dideoxynucleosides, polymerases, nucleases, transcriptases, ligases and restriction enzymes to alter at least a subset of said oligonucleotide probes. In a third step, the method provides for determining the molecular weight of at least the subset of altered probes by mass spectrometry and infering the sequence information of the sample polynucleotide therefrom.

12 Claims, 20 Drawing Sheets

OTHER PUBLICATIONS

Wetmur in Critical Reviews in Biochemistry and Molecular Biology 26:277–259 (1991) CRC Press. In. ed. Fasman.

Adamcyzk, J.J. Jr.; "Treatment of PCR products with shrimp alkaline phosphatase and exonuclease I: a reliable and fast method for obtaining DNA suitable for manual sequencing", USB Comments (company newsletter), 22:2, 36, 49 (1995).

Answorge, W. et al.; "A non–radioactive automated method for DNA sequence determination", Journal of Biochemical and Biophysical Methods, 13, 315–323 (1986).

Ballabio, A. et al.; "PCR test for cystic fibrosis deletion", Nature, 343, 220 (1990).

Benner, W.H. et al.; "Identification of Denatured Double–stranded DNA by Matrix–assisted Laser Desorption/Ionization Time–of–Flight Mass Spectrometry", Rapid Communications in Mass Spectrometry, 9, 537–540, (1995).

Ch'ang, L.Y. et al.; "Detection of ΔF508 Mutation of the Cystic Fibrosis Gene by Matrix–assisted Laser Desorption-Ionization Mass Spectrometry", Rapid Communications in Mass Spectrometry, 9, 772–774 (1995).

Chen, C.H. et al.; "Maldi for Fast DNA Analysis and Sequencing", LRA, 8, 87–99 (1996).

Chen, C.H., et al.; "Laser Desorption Mass Spectrometry For DNA Analysis And Sequencing", S.P.I.E., 2386, 13–23 (1995).

Chen, C.H.; "Mass Spectrometry High Speed DNA Fragment Sizing", Encyclopedia of Molecular Biology and Molecular Medicine, Ed. Myers R., vol. 4, 1–12 (1996).

Connell, C. et al.; "Automated DNA Sequence Analysis", Biotechniques, 5:4, 342–344 & 346–348 (1987).

Conner, B.J. et al.; "Detection of sickle cell $\beta^s$–globin allele by hybridization with synthetic oligonucleotides", Proc. Natl. Acad. Sci. USA, 80, 278–282 (1983).

Cotton, R.G.H. et al.; "Reactivity of cytosine and thymine in single–base–pair mismatches with hydroxylamine and osmium tetroxide and its application to the study of mutations", Proc. Natl. Acad. Sci. USA, 85, 4397–4401 (1988).

Doktycz, M.J. et al.; "Analysis of Polymerase Chain Reaction–Amplified DNA Products by Mass Spectrometry Using Matrix–Assisted Laser Desorption and Electrospray: Current Status", Analytical Biochemistry, 230, 205–214 (1995).

Eggerding, F.A.; "A One–step Coupled Amplification and Oligonucleotide Ligation Procedure for Multiplex Genetic Typing", PCR Methods and Applications, 4, 337–345 (1995).

Ehlen, T. et al.; "Detection of RAS Point Mutations By Polymerase Chain Reaction Using Mutation–Specific, m Inosine–Containing Oligonucleotide Primers", Biochemical and Biophysical Research Comununications, 160:2, 441–447 (1989).

Embury, S.H. et al.; "Rapid Prenatal Diagnosis Of Sickle Cell Anemia By A New Method Of DNA Analysis", New England Journal of Medicine, 316, 656–661 (1987).

Erlich, H.A. et al.; "Recent Advances in the Polymerase Chain Reaction", Science, 252, 1643–1651 (1991).

Fang, P. et al.; "Simultaneous Analysis of Mutant and Normal Alleles for Multiple Cystic Fibrosis Mutations by the Ligase Chain Reaction", Human Mutation, 6, 144–151 (1995).

Hata, A.M. et al.; "Direct detection and automated sequencing of individual alleles after electrophoretic strand separation: identification of a common nonsense mutation in exon 9 of the human lipoprotein lipase gene", Nucleic Acids. Research, 18:18, 5407–5411 (1990).

Huntkapiller, T. et al.; "Large–Scale and Automated DNA Sequence Determination", Science, 254, 59–67 (1991).

Jagadeeswaran, J. et al.; "Use of Reverse–Phase Chromatography in the Maxam–Gilbert Method of DNA Sequencing A Step Toward Automation", Gen Anal. Techn., 3, 79–85 (1986).

Jurinke, C. et al.; "Analysis of Ligase Chain Reaction Products via Matrix–Assisted Laser Desorption/Ionization Time–of–Flight–Mass Spectrometry", Analytical Biochemistry, 237, 174–181 (1996).

Kidd, V.J. et al.; "$\alpha_1$–Antitrypsin deficiency detection by direct analysis of the mutation in the gene", Nature, 304, 230–234 (1983).

Köster, H. et al.; "A strategy for rapid and efficient DNA sequencing by mass spectrometry", Nature Biotechnology, 14, 1123–1128 (1996).

Kuppuswamy, M.N. et al.; "Single nucleotide primer extension to detect genetic diseases: Experimental application to hemophilia B (factor LX)and cystic fibrosis genes", Proc. Natl. Acad. USA, 88, 1143–1147 (1991).

Liu, Y–H. et al.; "Rapid Screening of Genetic Polymorphisms Using Buccal Cell with Detection by Matrix–assisted Laser Desorption/Ionizsation Mass Spectrometry", Rapid Comm. Mass Spectrometry, 9, 735–743 (1995).

Limbach, P.A.; "Indirect Mass Spectrometric Methods For Characterizing And Sequencing Oligonucleotides", Mass Spectrometry Reviews, 15, 297–336 (1996).

Little, D. P. et al.; "Schemes for DNA Mutation Detection Using MALDI Mass Spectrometry", Desorption '96, Röbornholm, Denmark, Sep. 18–21, 1996, Abstract C14.

Maniatis, T et al.; "Molecular Cloning: A Laboratory Manual", Cold Spring Harbor Laboratory, 382–389 & 475–478 (1982).

Mathieu–Daudé, F. et al.; "DNA rehybridization during PCR: The '$C_o$effect' and its consequences", Nucleic Acids Research, 24, 2080 (1996) Abstract only.

Miki, Y. et al.; "A Strong Candidate for the Breast and Ovarian Cancer Susceptibility Gene BRCA1", Science, 266, 66–71 (1994).

Moores, J.C.; "Current Approaches to DNA Sequencing", Analytical Biochemistry, 163, 1–8 (1987).

Myers, R.M. et al.; "Mutation Detection by PCR, GC–Clamps, and Denaturing Gradient Gel Electrophoresis", PCR Technology, Stockton Press, 71–88 (1989).

Newton, C.R. et al.; "Analysis of any point mutation in DNA. The amplification refractory mutation system (ARMS)", Nucleic Acids Research, 17:7, 2503–2516 (1989).

Nickerson, D.A. et al.; "Automated DNA diagnostics using ELISA–based oligonucleotide ligation assay", Proc. Natl. Acad. Sci. USA, 87, 8923–8927 (1990).

Nikiforov, T.T. et al.; "Genetic Bit Analysis: a solid phase method for typing single nucleotide polymorphisms", Nucleic Acids Research, 22:20, 4167–4175 (1994).

Nyren, P. et al.; "Solid Phase DNA Minisequencing by an Enzymatic Luminometric Inorganic Pyrophosphate Detection Assay", Analytical Biochemistry, 208, 171–175 (1993).

Pieles, U. et al.; "Matix–assisted laser desorption ionization time–of–flight mass spectrometry: a powerful tool for the mass and sequence analysis of natural and modified oligonucleotides", Nucleic Acids Research, 21:14, 3191–3196 (1993).

Prober, J. M. et al.; "A System for Rapid DNA Sequencing wih Fluorescent Chain–Terminating Dideoxynucleotides", Science, 238, 336–341 (1987).

Roubi, M.; "Mass spectrometry is becoming a tool for genetic screening", Chemical & Engineering News, 74:48 52–54 (1996).

Roskey, M.T. et al.; "DNA sequencing by delayed extraction–matrix–assisted laser desorption/ionization time of flight mass spectrometry", Proc. Natl. Acad. Sci. USA, 93, 4724–4729 (1996).

Saiki, R.K. et al.; "Analysis of enzymatically amplified β–globin and HLA–Qα DNA with allele–specific oligonucleotide probes"; Nature, 324, 163–166 (1986).

Schuette, J.M. et al.; "Sequence analysis of phosphorothiate oligonucleotides via matrix–assisted laser desorption ionization time–of–flight mass spectrometry", Journal of Pharmaceutical and Biomedical Analysis, 13, 1195–1203 (1995).

Shaler, T.A. et al.; "Analysis of Enzymatic DNA Sequencing Reactions by Matrix–assisted Laser Desorption/Ionization Time–of–flight Mass Spectrometry"; Rapid Communications in Mass Spectrometry, 9, 942–947 (1995).

Smirnov, I.P. et al.; "Sequencing Oligonucleotide by Exonuclease Digestion and Delayed Extraction Matrix–Assisted Laser Desorption Ionization Time–of–Flight Mass Spectrometry", Analytical Biochemistry, 238, 19–25 (1996).

Syvänen, A–C. et al.; "A Primer–Guided Nucleotide Incorporation Assay in the Genotyping of Apolipoprotein E", Genomics, 8, 684–692 (1990).

Syvänen, A–C, et al.; "Identification of Individuals by Analysis of Biallelic DNA Markers, Using PCR and Solid–Phase Minisequencing", Am. J. Hum. Genet., 52, 46–59 (1993).

Taranenko, N.I. et al.; "Laser desorption mass spectrometry for point mutation detection", Genetic Analysis Biomolecular Engineering, 13, 87–94 (1996).

Tabor, S. et al.; "A single residue in DNA polymerases of the Escherichia coli DNA polymerase I family is critical for distinguishing between deoxy–and dideoxyribonucleotides", Proc. Natl. Acad. Sci. USA, 92, 6339–6343 (1995).

Vestal, M.L. et al.; "Delayed Extraction Matrix–assisted Laser Desorption Time–of–light Mass Spectrometry", Rapid Comm. in Mass Spect., 9, 1044–1050 (1995).

Werle, E. et al.; "Convenient single–step, one tube purification of PCR products for direct sequencing", Nucleic Acids Research, 22:20, 4354–4355 (1994).

Wu, D.Y. et al.; "The Ligation Amplification Reaction (LAR)—Amplification of Specific DNA Sequences Using Sequential Rounds of Template–Dependent Ligation", Genomics, 4, 560–569 (1989).

Samols, S. B. et al., Amersham Life Science 22(2):29–36 (1995).

METHODS FOR DETERMINING SEQUENCES INFORMATION IN POLYNUCLEOTIDES USING MASS SPECTROMETRY

FIELD OF THE INVENTION

The invention generally relates to methods for the determination of sequence information in polynucleotides and more specifically for the identification of nucleotide polymorphisms using mass spectrometry.

BACKGROUND OF THE INVENTION

Gene probe assays which depend upon the binding of DNA probes with their complementary base pairs on a target molecule are among the most common assays used by molecular biologists. Such assays require a great deal of time to bind the probe to a target DNA, to remove any excess unhybridized probe and to analyze the hybridized probe.

The time required to perform these assays and the difficulties associated in performing these assays make such assays inefficient in searching for single nucleotide polymorphisms (SNPs). An SNP is a change (deletion, insertion or substitution) in any single nucleotide base in the region of the genome of interest. Because SNPs occur so frequently in the human genome (about once in every 500 bases), SNPs are useful markers in studying the human genome.

The detection of SNPs is typically performed using automated DNA sequencers. However such sequencers are generally not well utilized in determining a single base change within a 500 base sequence. As a result an SNP search using a sequencer is slow and expensive.

The recent development of Matrix Assisted Laser Desorption Ionization Time of Flight Mass Spectrometry (MALDI-TOF MS) has permitted small amounts (about 5 femtomoles) of DNA to be analyzed to extreme resolution (one dalton accuracy). The sensitivity and mass resolution of MALDI-TOF mass spectrometry fall off with increasing mass, so that the current upper practical limit for analysis of DNA is between about 50 to 100 nucleotide bases. Samples of 500 nucleotide bases have been analyzed with MALDI-TOF but with poor resolution and sensitivity.

The present invention relates to a method for quickly determining polynucleotide sequences, with low labor intensity and a low cost per SNP assay.

SUMMARY OF THE INVENTION

In its broadest aspect, the invention provides a family of techniques for determining sequence information in polynucleotides by combining the recent disparate technologies of mass spectrometry and polynucleotide hybridization, amplification, extension and/or ligation techniques. Broadly, in a first step, the method for determining sequence information in a sample polynucleotide includes hybridizing with a sample polynucleotide one or a mixture of oligonucleotide probes having a nucleotide sequence complementary to a portion of the sample polynucleotide, thereby forming a complex. Then, in a second step, the complex is contacted with at least a member selected from the group consisting of nucleosides, dideoxynucleosides, polymerases, nucleases, transcriptases, ligases and restriction enzymes to alter at least a subset of said oligonucleotide probes. In a third step, the method provides for determining the molecular weight of at least the subset of altered probes by mass spectrometry and infering the sequence information of the sample polynucleotide therefrom.

In one embodiment the invention relates to a method for identifying a putative point mutation in a polynucleotide using mass spectrometry. The method includes hybridizing a primer to the polynucleotide having a putative point mutation such that the 3'-end of the primer is hybridized adjacent the putative point mutation; extending the 3'-end of the primer by adding a single nucleotide base matching the putative point mutation of the polynucleotide, thereby forming an extended primer; and identifying the added nucleotide base on the extended primer using mass spectrometry. In one embodiment the mass spectrometry used is matrix assisted laser desorption ionization time-of-flight (MALDI-TOF) mass spectrometry. In one embodiment the step of hybridizing the primer includes the steps of providing a primer having a sequence that hybridizes to a polynucleotide sequence next to a putative point mutation; heating the polynucleotide to a temperature sufficient to melt the polynucleotide; and cooling the polynucleotide to a temperature sufficient to hybridize the primer to the polynucleotide, thereby forming a duplex wherein the 3'-end of said primer is adjacent the putative point mutation. In one embodiment the step of extending includes providing at least one dideoxynucleoside triphosphate base (ddNTP) and providing a polymerase. In one embodiment, the polynucleotide is a DNA and the polymerase is a DNA polymerase. In another embodiment, the polynucleotide is an RNA and the polymerase is a reverse transcriptase.

Another embodiment of the invention exploites the use of a primer having a mass tag on the 5'-end of the primer. In one embodiment the mass tag is a thymidine DNA or polythymidylate segment, $T_n$, wherein n is an integer ranging from 1 to 40.

In yet another embodiment the invention relates to a multiplex method for identifying multiple putative point mutations in a polynucleotide using mass spectrometry. The method, in one embodiment, includes hybridizing a multiplicity of primers to a polynucleotide having multiple putative point mutations, the 3'-end of each primers being hybridized adjacent each putative point mutation; extending the 3'-end of each primers by adding a single nucleotide base to each primer, each single nucleotide base matching each putative point mutation of the polynucleotide, thereby forming a multiplicity of extended primers; and identifying the added nucleotide base on each extended primers using mass spectrometry. In one embodiment, the polynucleotide is a DNA and the polymerase is a DNA polymerase. In another embodiment, the polynucleotide is an RNA and the polymerase is a reverse transcriptase.

Another embodiment of the invention includes a method for identifying a putative point mutation in a DNA using mass spectrometry, including the step of hybridizing two oligonucleotide probes to a single stranded DNA having a putative point mutation such that the two probes together overlap the putative point mutation, ligating the two probes into a ligated single strand oligonucleotide only when the probe overlapping the putative point mutation has the nucleotide base complementary to the nucleotide base of the DNA at the putative point mutation and determining the identity of the nucleotide base matching the putative point mutation on the ligated oligonucleotide using mass spectrometry. In one embodiment the mass spectrometry is performed using matrix assisted laser desorption ionization time-of-flight (MALDI-TOF) mass spectrometry.

In still yet another embodiment the invention relates to a combinatorial method for determining sequence information in a region of a polynucleotide using mass spectrometry. In one embodiment the method includes, hybridizing a primer to a polynucleotide having a region of interest such that the 3'-end of the primer being hybridized is adjacent the region of interest and extending the 3'-end of the primer by adding a multiplicity of nucleotide bases matching the region of interest of the polynucleotide, thereby forming an extended primer. In one embodiment the extending step includes providing a multiplicity of nucleotide bases selected from the group consisting of deoxynucleoside triphosphate (dNTP) and dideoxynucleoside triphosphate (ddNTP), provided that at least one member of ddNTP is present, and providing a polymerase in a buffer solution. The identity of the added nucleotide bases on the extended primer is then determined using mass spectrometry. In one embodiment, the polynucleotide is a DNA and the polymerase is a DNA polymerase. In another embodiment, the polynucleotide is an RNA and the polymerase is a reverse transcriptase. In another embodiment the invention includes providing an exonuclease to the mixture resulting from the extension thereby producing a ladder sequence defining the mixture of extended primers. In one embodiment the exonuclease is selected from the group consisting of: phosphodiesterase type I, exonuclease I, exonuclease III, exonuclease V, exonuclease VII, and DNA polymerase III.

In another embodiment the invention relates to a multiplex combinatorial method for determining sequence information in multiple regions of a polynucleotide using mass spectrometry. The method includes hybridizing a multiplicity m of primers to a polynucleotide having multiple regions of interest such that the 3'-end of each of the primers is hybridized adjacent each region of interest, and extending the 3'-end of each of the primers by adding a multiplicity of nucleotide bases to each primer matching each region of interest of the polynucleotide, thereby forming a multiplicity of extended primers. In one embodiment the extension step includes providing a multiplicity of nucleotide bases selected from the group consisting of deoxynucleoside triphosphate (DNTP) and dideoxynucleoside triphosphate (ddNTP), provided that at least one member of ddNTP is present and providing a polymerase in a buffer solution. In one embodiment, the polynucleotide is a DNA and the polymerase is a DNA polymerase. In another embodiment, the polynucleotide is an RNA and the polymerase is a reverse transcriptase. The identity of the added nucleotide bases on each extended primers is determined using mass spectrometry.

BRIEF DESCRIPTION OF THE DRAWINGS

The foregoing and other objects, features and advantages of the present invention, as well as the invention itself, will be more fully understood from the following description of preferred embodiments, when read together with the accompanying drawings, in which:

FIG. 6b is a mass spectrum of the results of the multiplex assay performed in the presence of the five primers whose mass spectrum is shown in FIG. 6a;

DETAILED DESCRIPTION OF THE INVENTION

In its broadest aspect, the invention provides a family of techniques for determining sequence information in polynucleotides by combining the recent disparate technologies of mass spectrometry and polynucleotide hybridization, amplification, extension and/or ligation techniques. Broadly, in a first step, the method for determining sequence information in a sample polynucleotide includes hybridizing with a sample polynucleotide one or a mixture of oligonucleotide probes having a nucleotide sequence complementary to a portion of the sample polynucleotide, thereby forming a complex. Then, in a second step, the complex is contacted with a member selected from the group consisting of nucleosides, dideoxynucleosides, polymerases, nucleases, transcriptases, ligases and restriction enzymes to alter at least a subset of said oligonucleotide probes. In a third step, the method provides for determining the molecular weight of at least the subset of altered probes by mass spectrometry and infering the sequence information of the sample polynucleotide therefrom.

The invention also relates to methods for the identification of nucleotide polymorphisms using mass spectrometry. In the following detailed description of the invention, the terms "putative point mutation" or "single nucleotide polymorphism" are used interchangeably and are intended to mean any modification in a polynucleotide sequence which result in a single nucleotide base mutation, such as an insertion, a deletion or a substitution of a single nucleotide base. The term "putative mutation site" is intended to mean any modificationsin a polynucleotide sequence which results in a mutation of multiple nucleotide bases, resulting from an insertion, a deletion or a substitution of multiple nucleotide bases or combination thereof. The term "region" is intended to mean a portion of the sequence of a polynucleotide.

Figure 1:
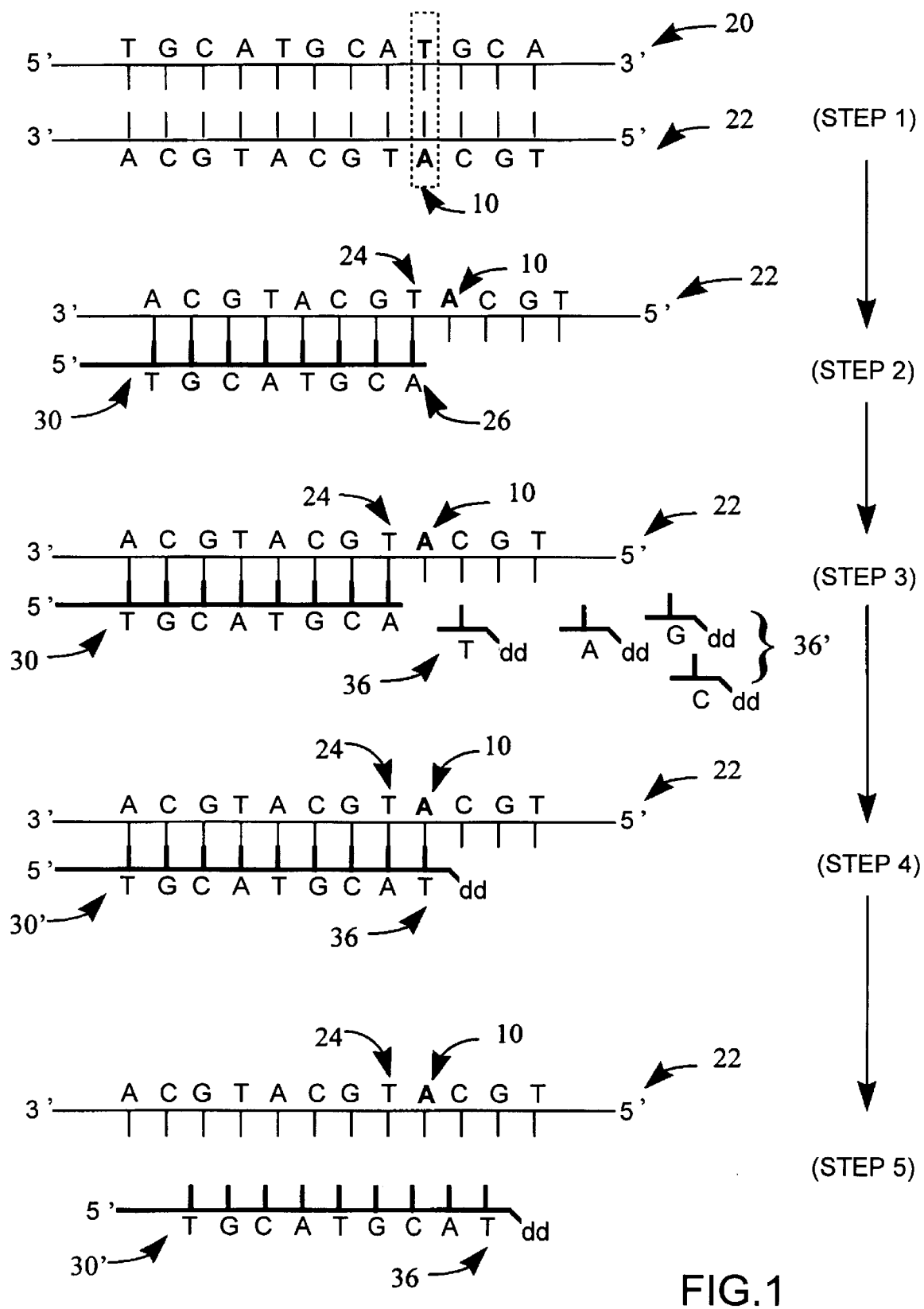
FIG. 1 is a highly schematic diagram of an embodiment of the method for identifying a single putative point mutation or polymorphic site in a DNA using PCR.

In brief overview and referring to FIG. 1, in one embodiment, the process of identifying a putative single point mutation 10 in a DNA 20 includes first (Step 1) separating the strands of the double stranded DNA into two single strands; one of which being a target strand 22 having the putative point mutation 10 of interest. Next (Step 2) a primer sequence 30 having a sequence of bases which is complementary to the bases on the target strand 22 up to and including the base 24 adjacent the putative point mutation 10 is annealed to the target strand 22.

Each of the possible complementary bases 36, 36', in the form of dideoxynucleotides, is added (Step 3) along with a DNA polymerase to the primer-target DNA complex. The dideoxynucleotide base 36 which is complementary to the putative point mutation 10 is incorporated into the primer sequence 30 (Step 4) to form an extended primer 30'. Because the primer 30' is now terminated with a dideoxynucleotide base 36, no further additions are possible.

The primer sequence 30' with the added dideoxynucleotide base 36 is next analyzed with a mass spectrometer (Step 5). Note that when using MALDI-TOF mass spectrometry, the primer-target DNA complex will fully dissociate under the laser desorption ionization process of the MALDI-TOF mass measurement. The mass of the primer 30' with the additional mass of the dideoxynucleotide base 36 is determined (comparative mass shown in Table 1), and, by subtracting the original mass of the primer 30, the mass of the dideoxynucleotide base 36 and, hence, the type of dideoxynucleotide base 36 are determined. By knowing the identity of the added dideoxynucleotide base 36, the identity of the complementary putative point mutation 10 is therefore deduced according to the rules of Watson-Crick base pairing.

TABLE 1

Dideoxy and Deoxy-Nucleotide bases

| Dideoxy Base | Formulae | Mass | Deoxy Base | Formulae | Mass |
| --- | --- | --- | --- | --- | --- |
| -ddC | $C_9H_{12}N_3O_5P$ | 273.155 | -dC | $C_9H_{12}N_3O_6P$ | 289.184 |
| -ddT | $C_{10}H_{13}N_2O_6P$ | 288.196 | -dT | $C_{10}H_{13}N_2O_7P$ | 304.195 |
| -ddA | $C_{10}H_{12}N_5O_4P$ | 297.210 | -dA | $C_{10}H_{12}N_5O_5P$ | 313.209 |
| -ddG | $C_{10}H_{12}N_5O_5P$ | 313.209 | -dG | $C_{10}H_{12}N_5O_6P$ | 329.208 |

In more detail, the DNA 20 is denatured (Step 1) and the two strands of DNA 20, e.g., separated by heating the native DNA to about 90°–99° C. for 10 to 60 seconds. The primer 30 is then added at a concentration ranging from about, e.g., 0.1 $\mu$M to about 10 $\mu$M, preferably 1 $\mu$M. The primer 30 preferably includes 15–50 nucleotide bases and is oriented such that the base 26, complementary to the base 24 adjacent the putative point mutation 10 on the target strand of DNA 22, is located at the 3' end of the primer 30. The mixture of primer 30 and target DNA 22 is cooled to between 37° to 72° C. to permit the annealing and hybridizing of the primer 30 to the target DNA 22 (Step 2). The next step (Step 3) consists of adding dideoxynucleotide bases 36, 36', a polymerase, and an appropriate buffer to the mixture in order to extend the 3'end of the primer 30 bound to the target DNA 22. This step is accomplished using standard DNA polymerase technology. The base 36 which is added to the primer 30 will be complementary to the putative point mutation 10 (Step 4).

In certain embodiments, the addition of a dideoxynucleotide base 36 to the primer 30 is performed using a thermostable DNA polymerase, for example Taq polymerase, AmpliTaq FS or a Taq DNA polymerase modified at position 667, Thermo Sequence™, or alternatively by using an ordinary thermostable DNA polymerase, such as Klenow, T7, or Sequenase DNA polymerase. Preferably, a Taq DNA polymerase modified at position 667, Thermo Sequenase ™, is used. By using a thermostable polymerase, the assay, in one embodiment, involves primer extension amplification by repeating cycles of: 1) DNA denaturation by heating above the melting point of the DNA sample; 2) annealing or hybridizing the primer to the DNA by cooling to the adequate temperature; and 3) extending the primer by adding a nucleotide base. Such amplification increases the molecular ratio of the extended primer 30'over the DNA sample. This will also result in an increase in sensitivity of the assay which permits detection of a polymorphic site on a DNA sample having a picomolar concentration (pM). However, when an ordinary thermolabile DNA polymerase is used, generally only one thermal cycle is possible because the activity of these enzymes is lost during the denaturation step unless fresh enzyme is added at each thermal cycle.

The number of thermal cycles necessary for primer extension amplification in any one assay is dependent on the initial concentration of the DNA sample and the sensitivity threshold of the mass spectrometer. In any one thermal cycle, the maximum increase in molar concentration of the extended primer is equal to the molar concentration of the DNA sample, assuming that all other components, i.e. primer 30 and nucleotide bases 36,36', are present in excess. The concentration of the extended primer will increase by one fold at every thermal cycle (the fold unit being the concentration of the DNA sample). In certain embodiments, where the concentration of the DNA sample is below the sensitivity threshold of the mass spectrometer, a large excess of primer over the DNA sample is used in combination with several thermal cycles in order to bring the concentration level of the extended primer above the threshold sensitivity of the mass spectrometer. At such time the molecular ratio of the primer 30 to DNA 20 ranges from about 1:1 to about 50:1 when up to 50 thermal cycles are used, and preferably from about 1:1 to about 25:1 when up to 25 thermal cycles are used.

The buffer used in combination with the polymerase is a buffer compatible with primer extension technology. However the use of a buffer containing an alkali metal generates DNA adducts which complicate the interpretation of the mass spectra, and thus renders the identification of the polymorphism more difficult. In a preferred embodiment, the buffer is a volatile acid-base combination which does not form DNA adducts. In preferred embodiments, the buffer is ammonium acetate or ammonium formate. In another preferred embodiment, the buffer is ammonium acetate in concentration ranging from 25 mM to 100 mM. In other preferred embodiments, the buffer includes a polymerase co-factor such as magnesium chloride or magnesium acetate. In a most preferred embodiment, the buffer is composed of 25–100 mM ammonium acetate with 1.5 mM magnesium acetate.

Once the primer has been extended, the identity of the added nucleotide base 36 is then determined (Step 5) by mass spectrometry by comparing the masses of the extended primer 30' and the primer 30. The mass difference between the two primers will be characteristic of the specific nucleotide base 36 which has been added to the primer 30' (see Table 1). Having determined the identity of the nucleotide base 36 on the extended primer 30', the identity of the nucleotide base at the putative point mutation 10 on the DNA 22 is then easily deduced according to the rules of Watson-Crick base pairing. In one embodiment, mass spectrometry analysis is carried out using electrospray, matrix assisted laser desorption ionization (MALDI), fast atom bombardment ionization (FAB) or plasma desorption ionization. In other embodiments, the mass spectrometry analysis is carried out using time-of-flight (TOF), quadruple, ion trap and sector analysis modes. In a preferred embodiment, mass spectrometry analysis is carried out using MALDI-TOF mass spectrometry.

Figure 2:
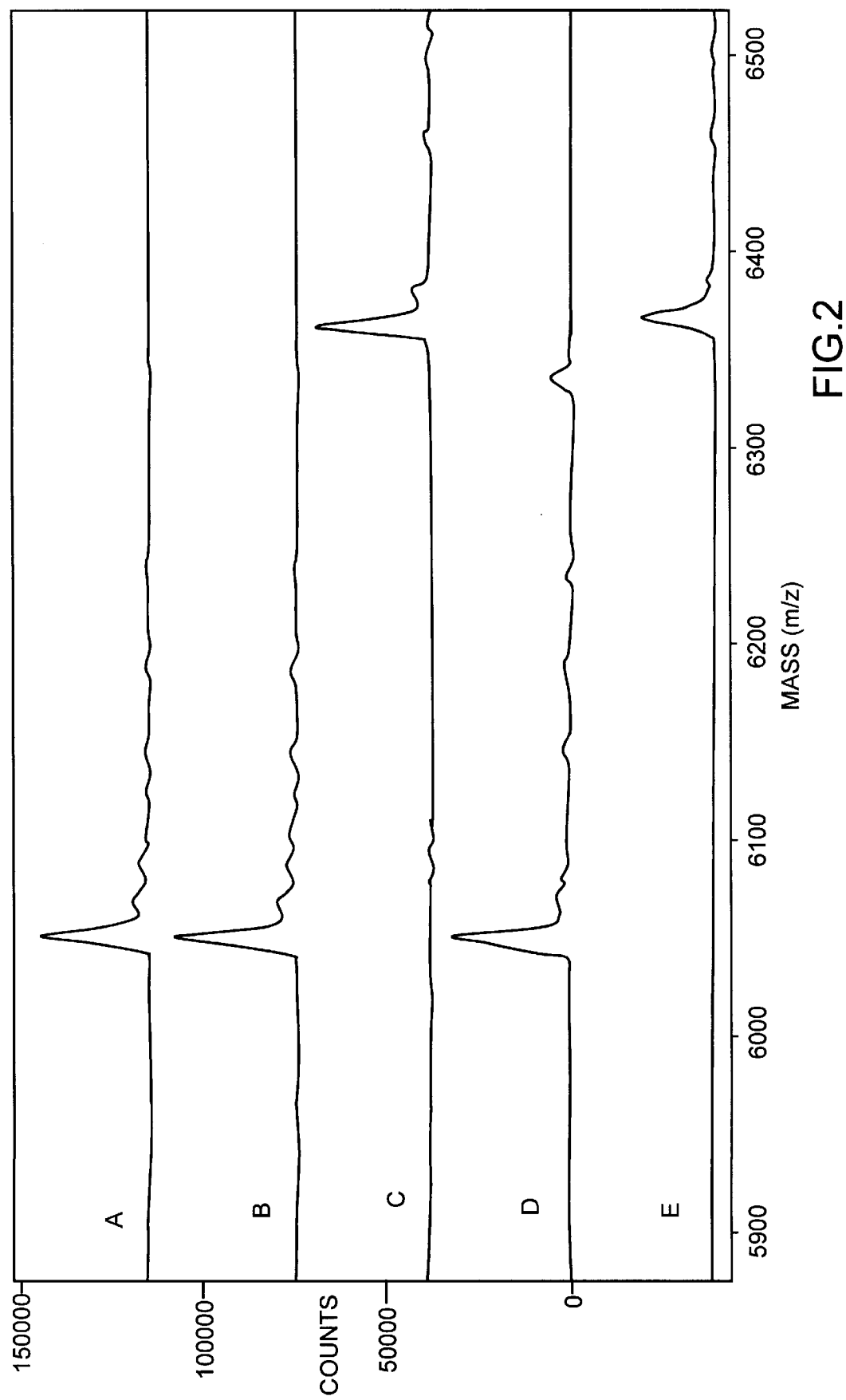
FIG. 2 depicts the results of a single nucleotide polymorphism (SNP) assay using primer extension reaction with: ddA, line A; ddC, line B; ddG, line C; ddT, line D; and the four ddNTPs, line E.

Referring to FIG. 2, the results of a single nucleotide polymorphism (SNP) assay using primer extension reaction with polymerase is shown. For this experiment, the target DNA consisted of the sequence lacI (wild type "C") 5'-CTGAATTACA TTCCCAACCG CGTGGCACAA CAACTGGCGG GCAAACAGTC GTTGCTGATT-3'(SEQ ID NO:1), where C represents the putative point mutation 10. For the purpose of primer extension amplification, Thermosequenase™, a genetically altered form of Taq DNA polymerase, available from Amersham Life Science (Arlington Heights, Ill., USA) was used to repeatedly extend the primer 3'- TTGACCGCCC GTTTGTCAGC-5'(SEQ ID NO:2). The primer was present in 2.5× molar excess over the target DNA and it was determined that about one half of the primer was converted in a single thermal cycle of 95° C. for 10 sec., 37° C. for 60 sec., and 72° C. for 60 sec. Substantially all of the primer was extended in three cycles. As is shown in FIG. 2, when dideoxyadenosine triphosphate (ddATP) (line A), and dideoxycytidine triphosphate (ddCTP) (line B) were individually added as the base 36', substantially none of the added dideoxynucleotide base was incorporated into the primer 30. When dideoxyguanosine triphosphate (dGTP) (line C) was added as the base, the primer 30 was all converted to the extended primer 30' having an additional dideoxyguanylate (ddG) base. When dideoxythyminidine triphosphate (dTTP) was added as the base (line D) a small portion of the dideoxythymidylate base (ddT) was non specifically added to the primer. However, when all four dideoxynucleotides (line E) were added together, again only the dideoxyguanylate was incorporated into the primer.

Figure 3:
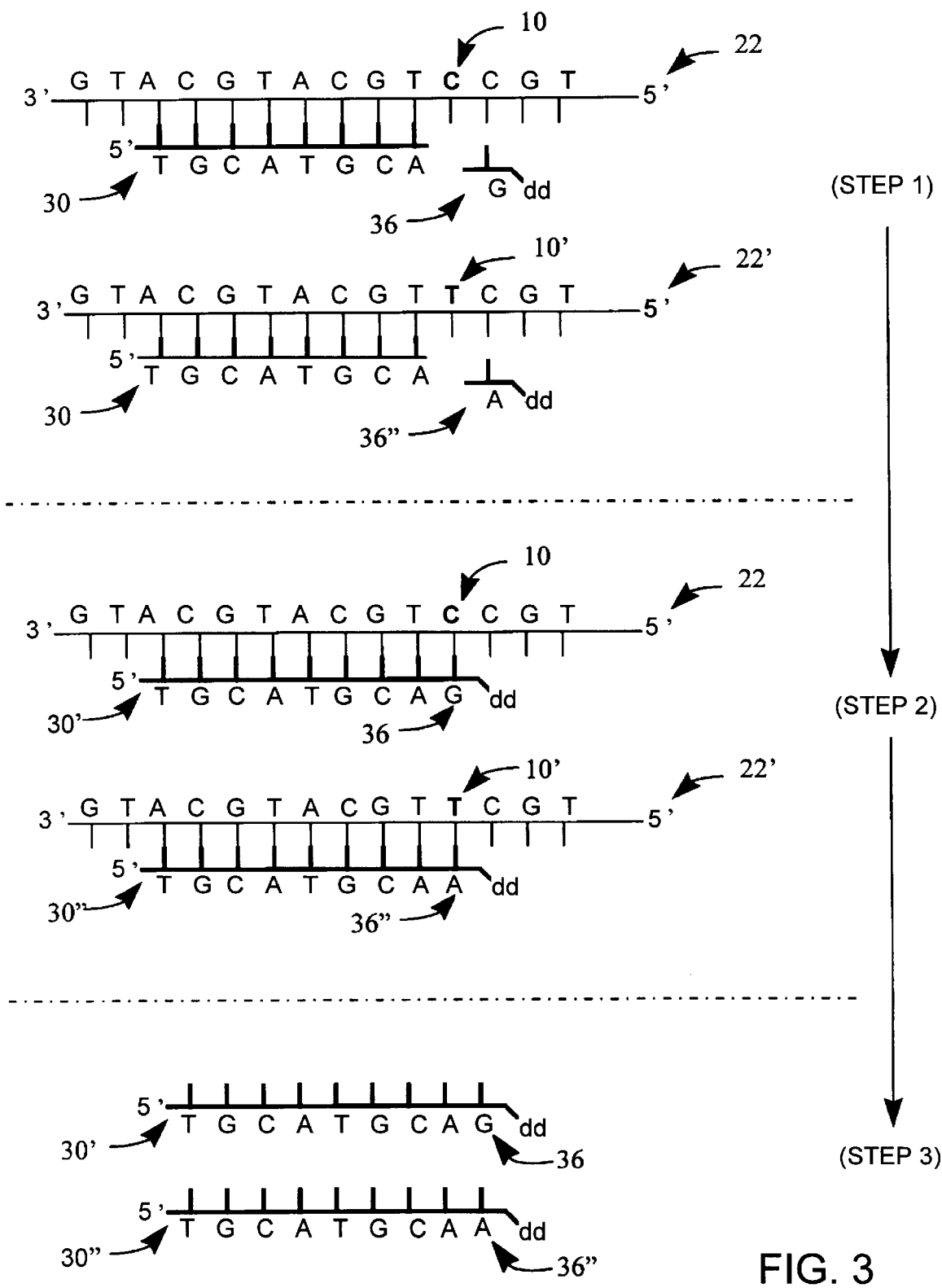
FIG. 3 is a highly schematic diagram of an embodiment of the assay used to determine heterozygous single nucleotide polymorphisms.
Figure 4:
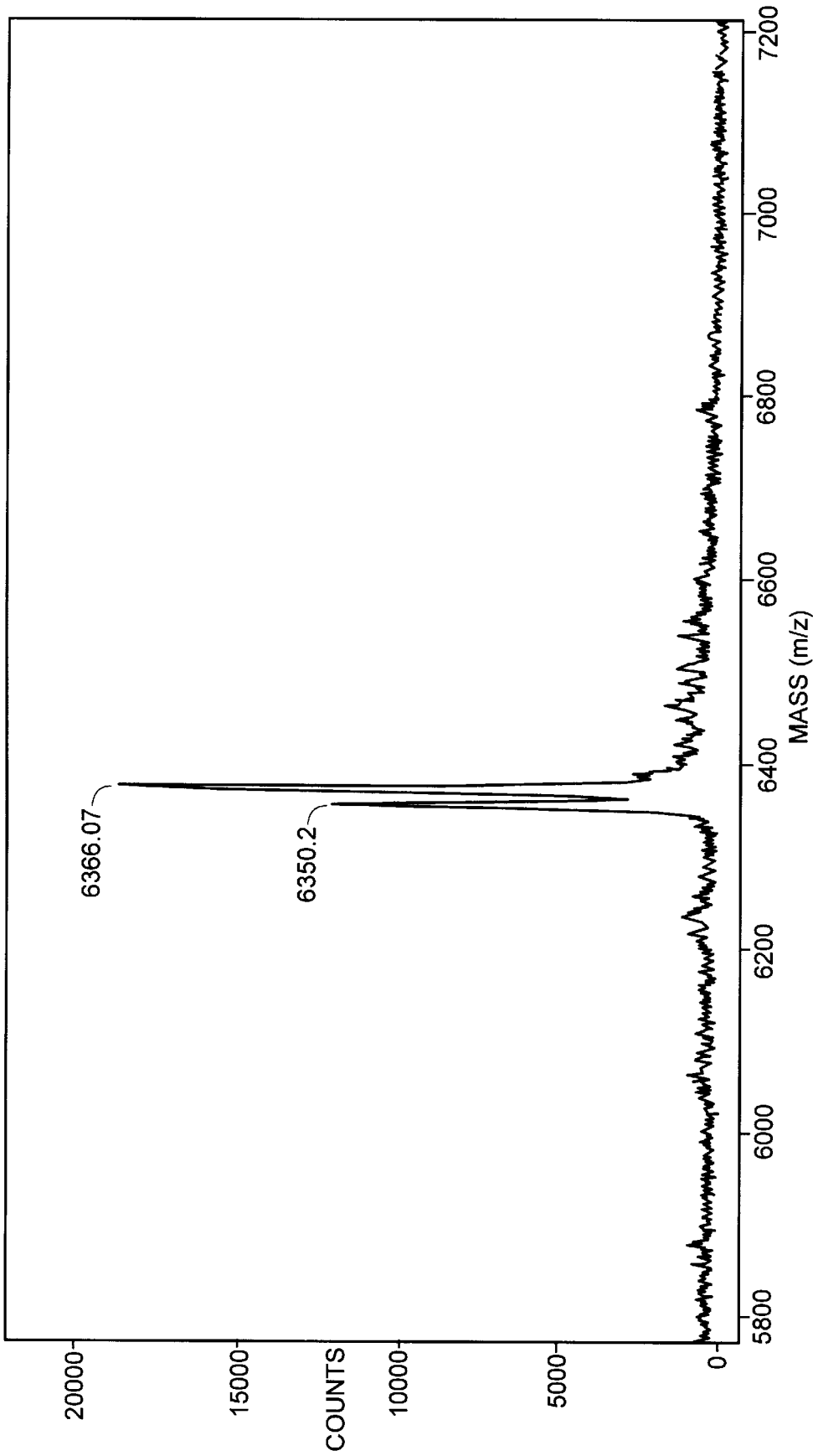
FIG. 4 is a diagram of a mass spectrum of the results of a single nucleotide polymorphism assay performed, in the presence of all four ddNTPs, on an heterozygous sample having C and T at the variable site.

Referring to FIG. 3, when the method is used to investigate single nucleotide polymorphisms in a heterozygous sample, the DNA strands 22, 22' of the heterozygous sample contain each a different nucleotide base 10 and 10', respectively, at the putative point mutation. In the example shown, the sample contain a 1:1 mixture of DNA target having cytosine or thymine at the putative point mutations 10, 10' respectively. As discussed above the DNA is denatured and each of the target strands 22, 22' hybridized with a primer 30 (Step 1). The four dideoxynucleotide bases are then added along with the polymerase and buffer, as discussed above. The dideoxynucleotide bases 36, 36" which are complementary to the putative point mutations 10, 10', respectively, thereby extend the primer 30 (Step 2). In the example shown, the primer 30 hybridized with the target DNA 22 and 22' is extended by dideoxyguanylate (ddG) 36 and dideoxyadenylate (ddA) 36", respectively. Referring to FIG. 4, when analyzed by mass spectroscopy as described above, the result is a mass spectrum having two peaks which differ by a mass of 16.050 Da which is close to the expected molecular weight difference of 15.999 Da between the two dideoxynucleotide bases dG and dA which extend each primer 30' and 30" and which is within the experimental error of the mass spectrometer.

Figure 5:
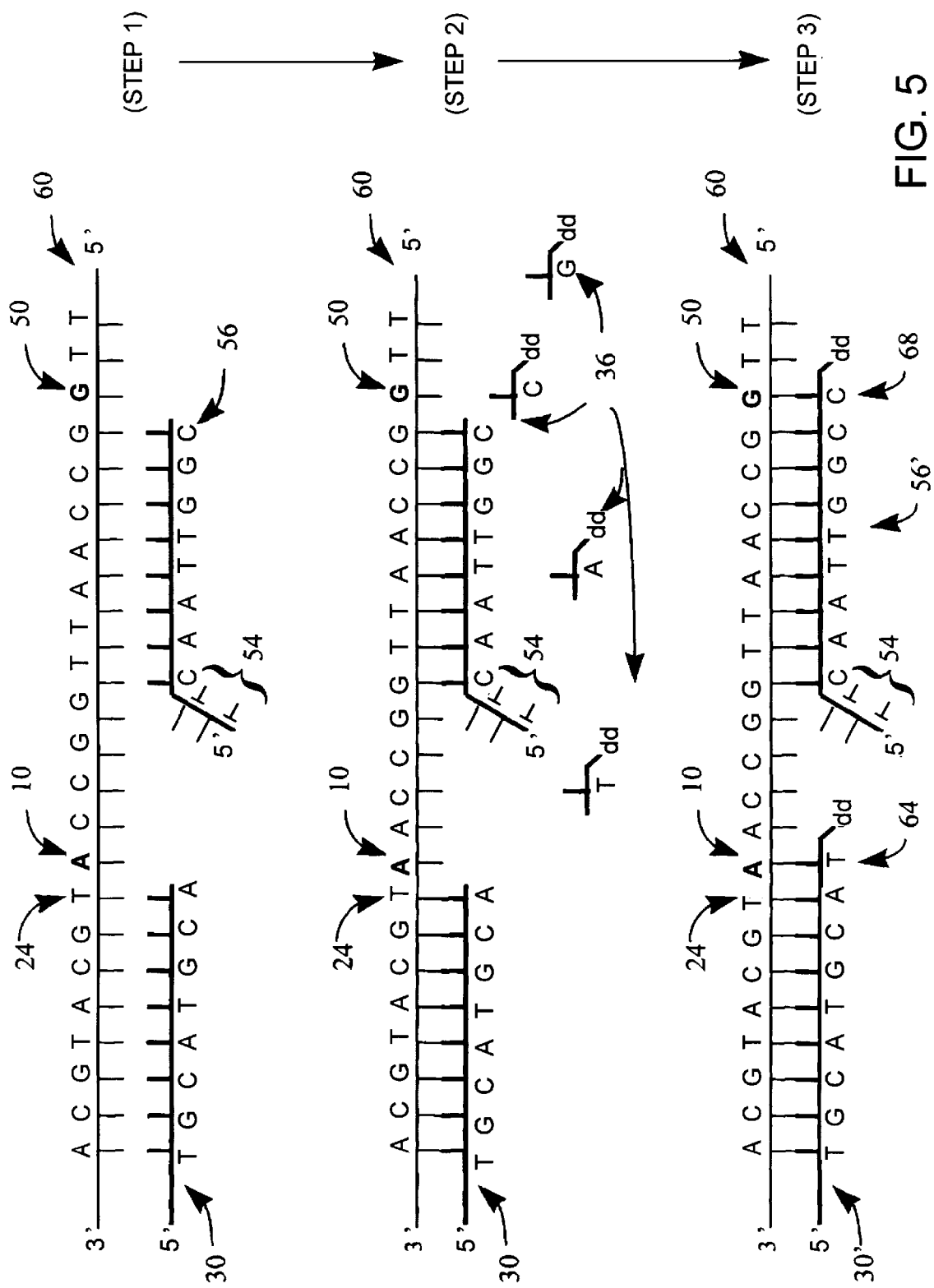
FIG. 5 is a highly schematic diagram of an embodiment of an assay used to determine multiple single nucleotide polymorphisms using mass tags.

In another embodiment and referring to FIG. 5, the primer 56 includes a mass tag 54. The mass tag 54 is preferably any form of mass extension to the primer 56 which does not hybridize with the target DNA 60 and which also does not interfere with the stability of the hybrid or interfere with the extension of the primer using DNA polymerase. Thus in one embodiment the mass tag 54 is constructed of two or more nucleotide bases 54, added to the 5' end of the primer 56, which are not complementary to the target DNA 60. For convenience of synthesis, the mass tag 54 may consist of a homopolymer tail 54 synthesized to the 5' end of the primer 56. In one embodiment the homopolymer tail 54 is a poly-deoxythymidylate, $T_n$ wherein n is an integer ranging from 1 to 40.

The purpose of the mass tag is to separate the primers and the extended primers which might otherwise be unresolvable by mass spectrometry. Thus, two primers or extended primers may have the same number of bases and hence have approximately the same molecular weight and therefore be unresolvable by mass spectrometry, the addition of a mass tag to one of the primers adds sufficient mass to permit them to be resolved. This permits two or more primers to be used in the same assay to probe for multiple single nucleotide polymorphisms simultaneously.

To perform such an assay, probing for two single nucleotide polymorphisms for example, two primers 30, 56 are provided (Step 1) which are each respectively complementary to the bases adjacent the two different single nucleotide polymorphisms 10, 50, shown on a single target strand of DNA 60. The primers 30, 56 differ in mass by at least the addition of a mass tag 54 to one of the primers 56. As described previously, each primer 30, 56 is hybridized to its complementary region of the target DNA 60 and the dideoxynucleotide bases 36, polymerase and buffer (not shown) are added to the mixture (Step 2). Each dideoxynucleotide base 64, 68 which is complementary to its respective single nucleotide polymorphism 10, 50 then elongates the primer 30, 56 respectively (Step 3) as described above. The target DNA 60 and the primers 30, 56, which have been elongated by the bases 64, 68 respectively, are analyzed by mass spectrometry as described previously.

The multiple SNP assay applies equally well if the SNPs are located on the same DNA segment but different loci, or on two or several DNA segments. The several DNA segments may be complementary strands or have fully distinct nucleotide sequences. Some assays may be designed such that the primers hybridize on either one or the other of the two complementary DNA strands to be probed. This is particularly well suited to multiplex assay experiments where two SNPs are separated from each other by a number of nucleotide bases smaller than the number of nucleotide bases of the downstream primers thereby avoiding overlapping of their binding site on the DNA. Since the 3' ends of the sequences of two complementary DNA strands run opposite to each other, it is possible to design two primers to probe two SNPs close to each other so that one primer binds on one strand of DNA and the downstream one binds on the other strand, each having their 5'-end extending away from the two putative point mutations and their 3' end adjacent one putative point mutation and such that the primers have no complementary segments in their sequences.

Figure 6A:
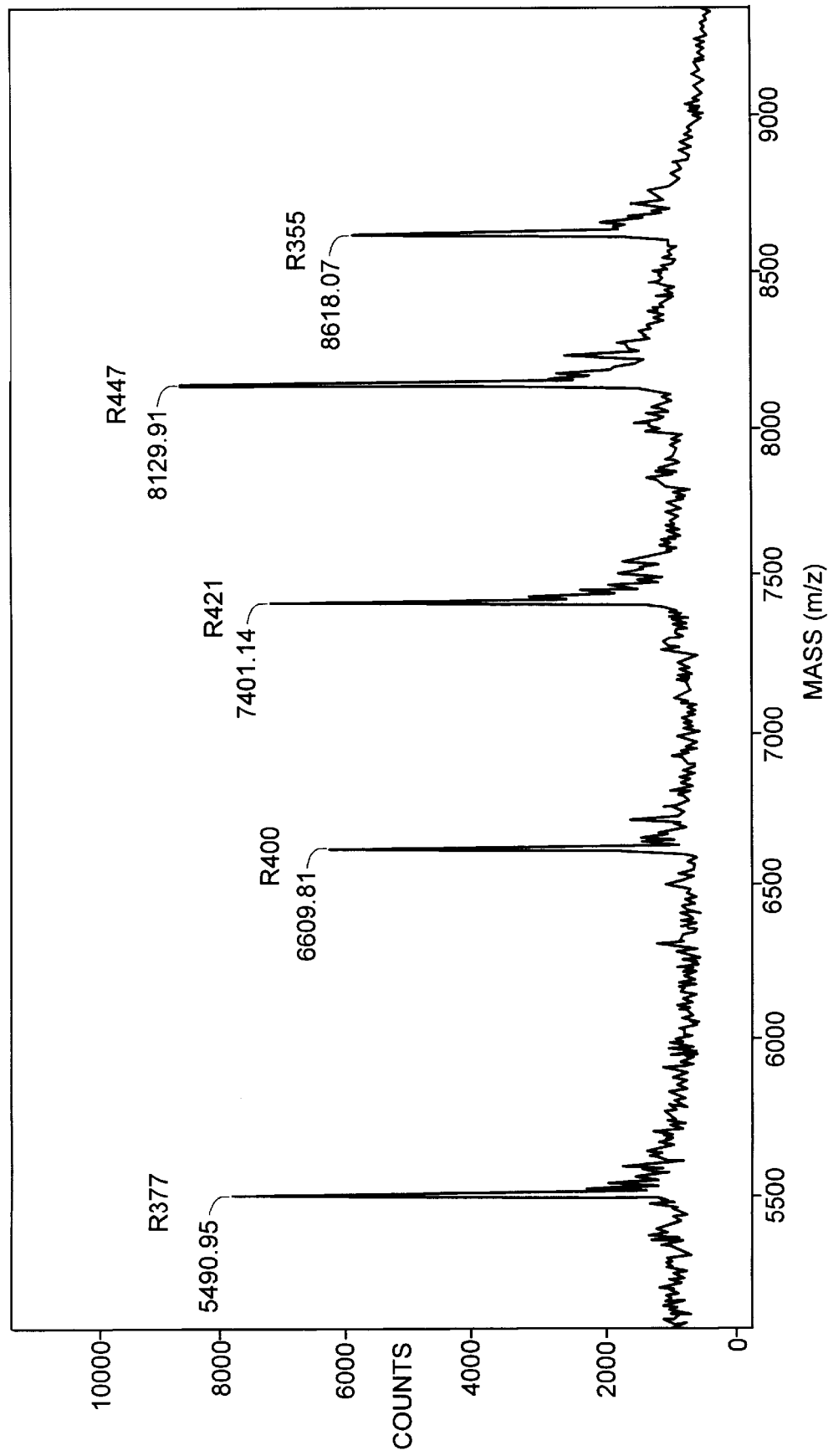
FIG. 6a is a mass spectrum of five primers having mass tags used in performing a multiplex single nucleotide polymorphism assay for BRCA1 single point mutations R355, R377, R400, R421, and R447.
Figure 6B:
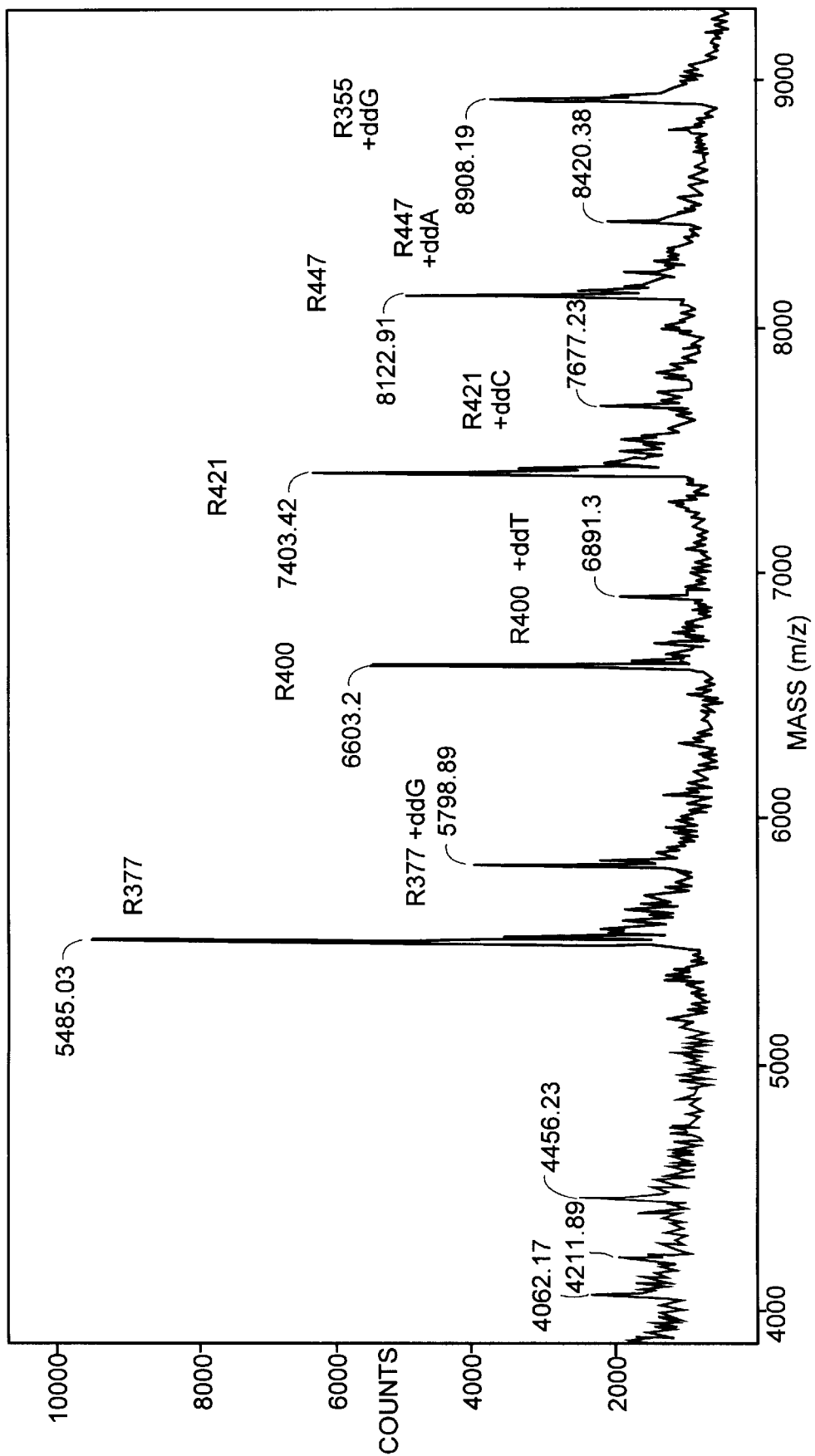

The results of such multiple single nucleotide polymorphism assays are shown in FIGS. 6a, 6b, 6c, 6d, 6e and 6f. In FIG. 6a and 6b, the experiment depicts five primers (R377, R400, R421, R447, R355) designed to examine five loci on the breast cancer susceptibility gene BRCA1. As shown in Table 2 below, the five primers are each complementary to a different region of the gene. Each primer has the same core length of eighteen complementary bases but each primer but one has a different mass tag from the others; one primer having no mass tag. Therefore, each primer has a significantly different mass from all the other primers. The mass spectra of the five primers before extension are shown in FIG. 6a. When the primers are extended using the method described above with twenty five thermal cycles and the mass spectra taken, the mass of each primer is increased by the mass of the added nucleotide. Note that primer R355 was entirely converted by the addition of dideoxyguanine and as such there is no peak in FIG. 6b corresponding to the unelongated primer. Unexpectedly, the addition of a decadeoxythymidylate residue ($dT_{10}$) on the 5' end of R3355 did not appear to interfere with the extension of primer R377 even though the two primers anneal to the DNA within a couple of nucleotide bases.

Figure 6C:
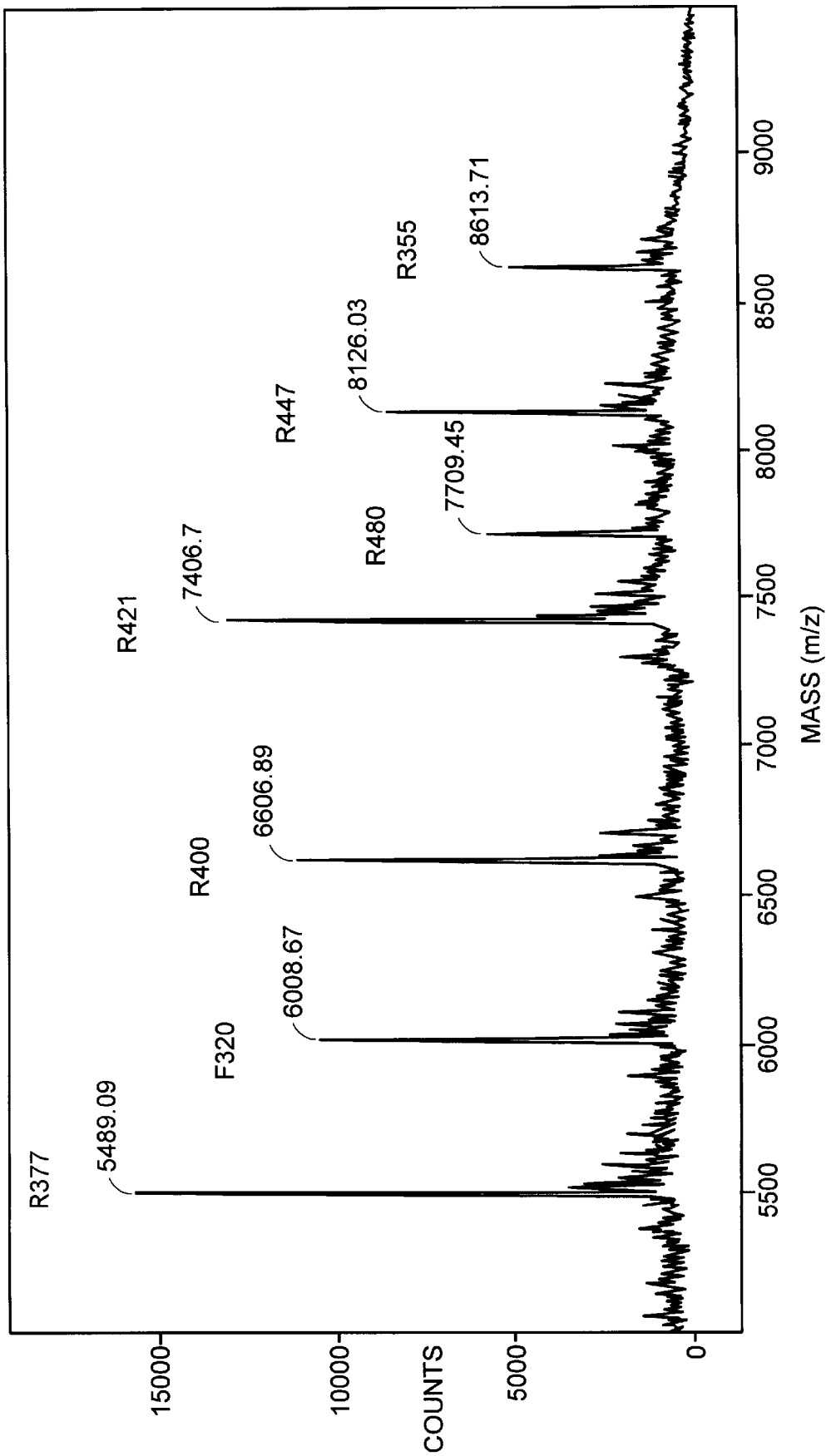
FIG. 6c is a mass spectrum of seven primers having mass tags used in performing a multiplex single nucleotide polymorphism assay for BRCA1 single point mutations F320, R355, R377, R400, R421, R480 and R447.
Figure 6D:
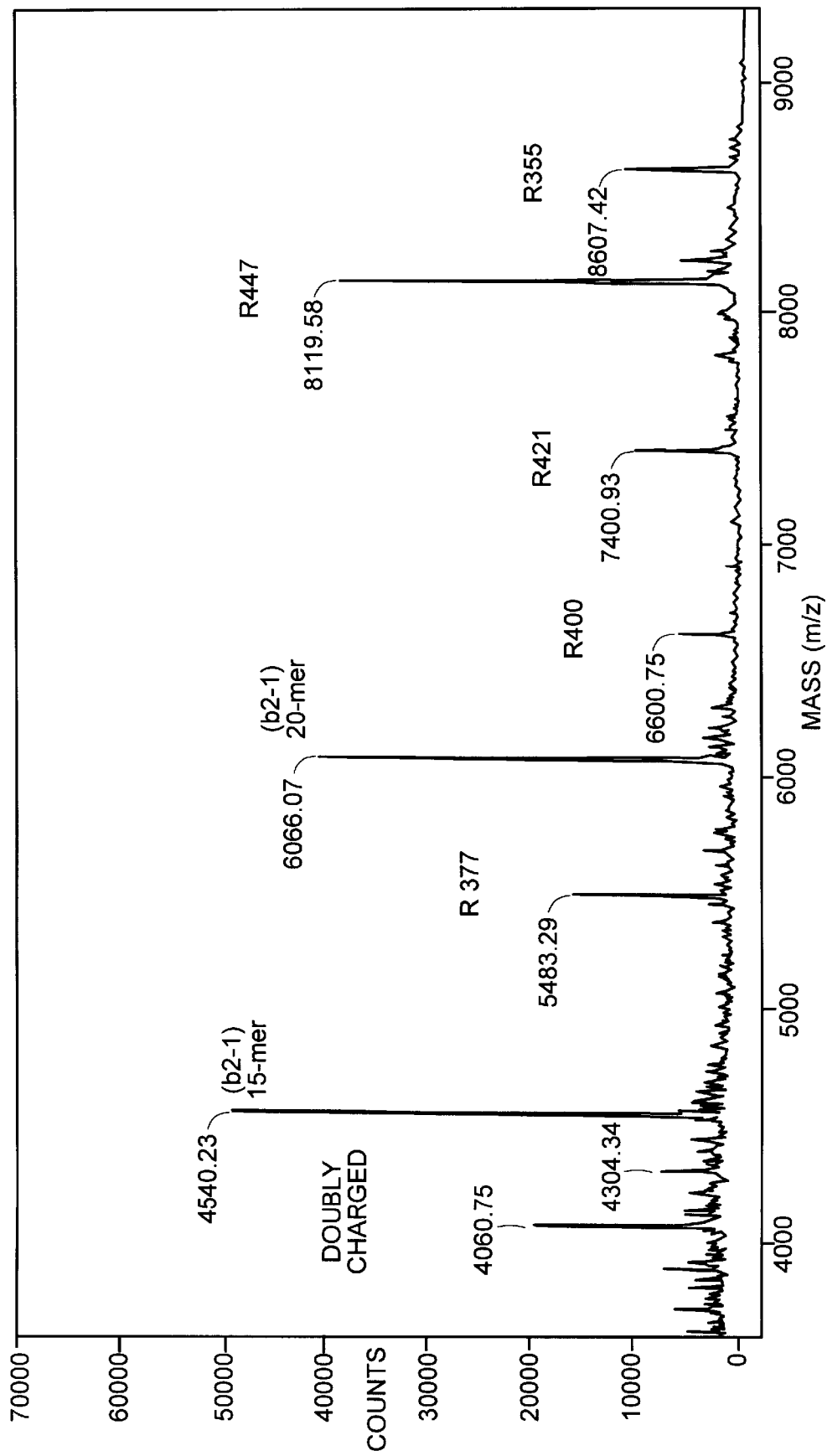
FIG. 6d is a mass spectrum of the results of the multiplex assay performed in the presence of the seven primers whose mass spectrum is shown in FIG. 6c.

FIGS. 6c and 6d depict an experiment with seven primers designed to examine seven loci on the breast cancer susceptibility gene BRCA1 (1355, R377, R400, R421, R447, R480 on one strand and F320 on the other strand). All the primers, shown in FIG. 6c, were extended by the expected nucleotide bases within twenty five thermal cycles. In FIG. 6d, all fourteen peaks of the seven primers and the seven extended primers were resolved, but two primers, R355 and F320, were nearly quantitatively extended. Note that primer F320 gave two products: one corresponding to the addition of ddT and the other corresponding to the addition of dT and ddC. T and C matches the two nucleotides bases downstream of the binding site of primer F320 on BRCA1. This two-base extension is due to carry-over of residual deoxynucleotide bases from PCR amplification of target DNA BRCA1. Residual deoxynucleotide bases can be eliminated by purification of DNA target after PCR amplification by ethanol precipitation, gel filtration, or incubation with shrimp alkaline phosphatase.

Figure 6E:
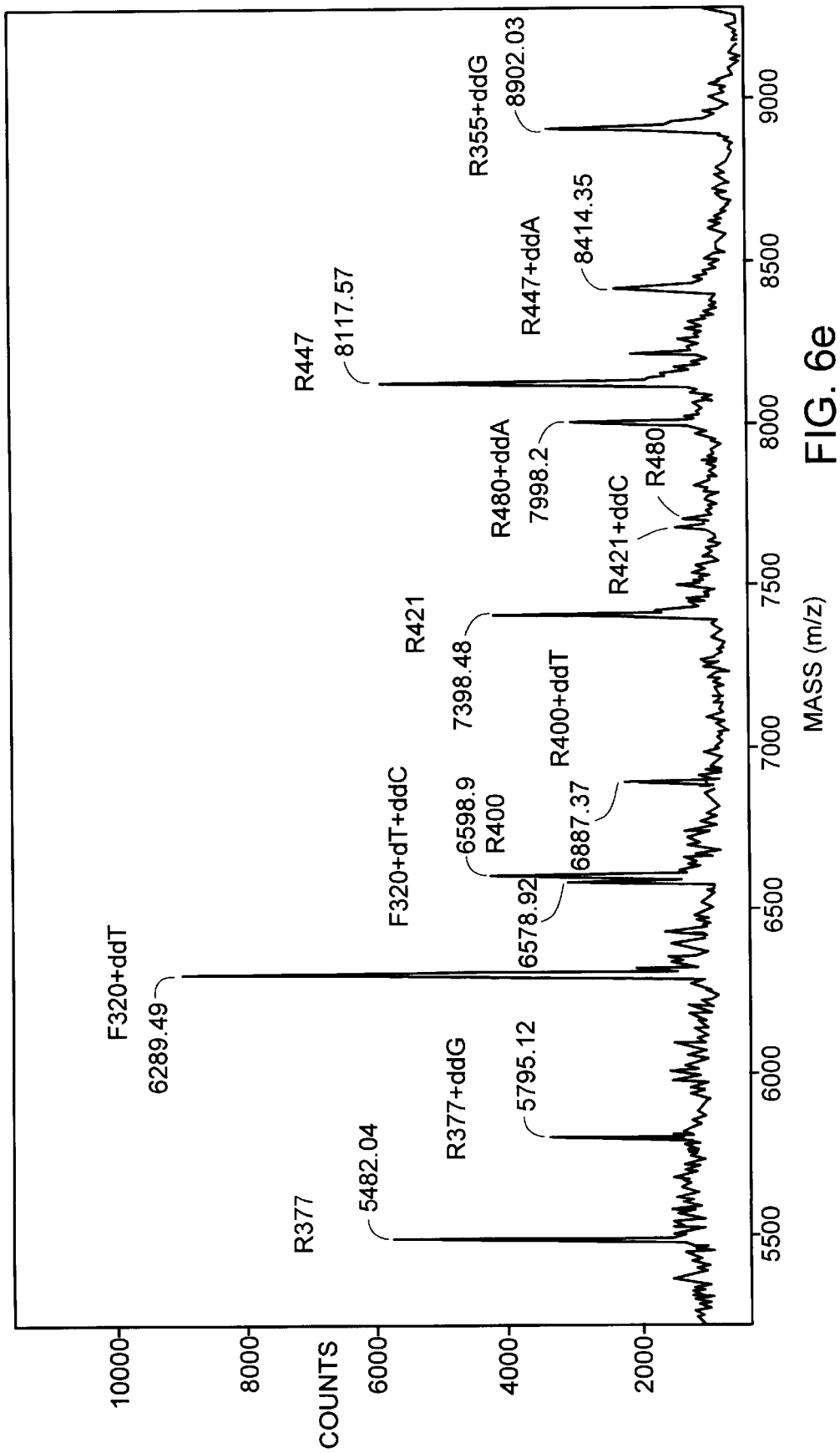
FIG. 6e is a mass spectrum of seven primers having mass tags used in performing a multiplex single nucleotide polymorphism assay for BRCA1 single point mutations R355, R377, R400, R421, and R447 and for lacz single point mutation (b2-1)
Figure 6F:
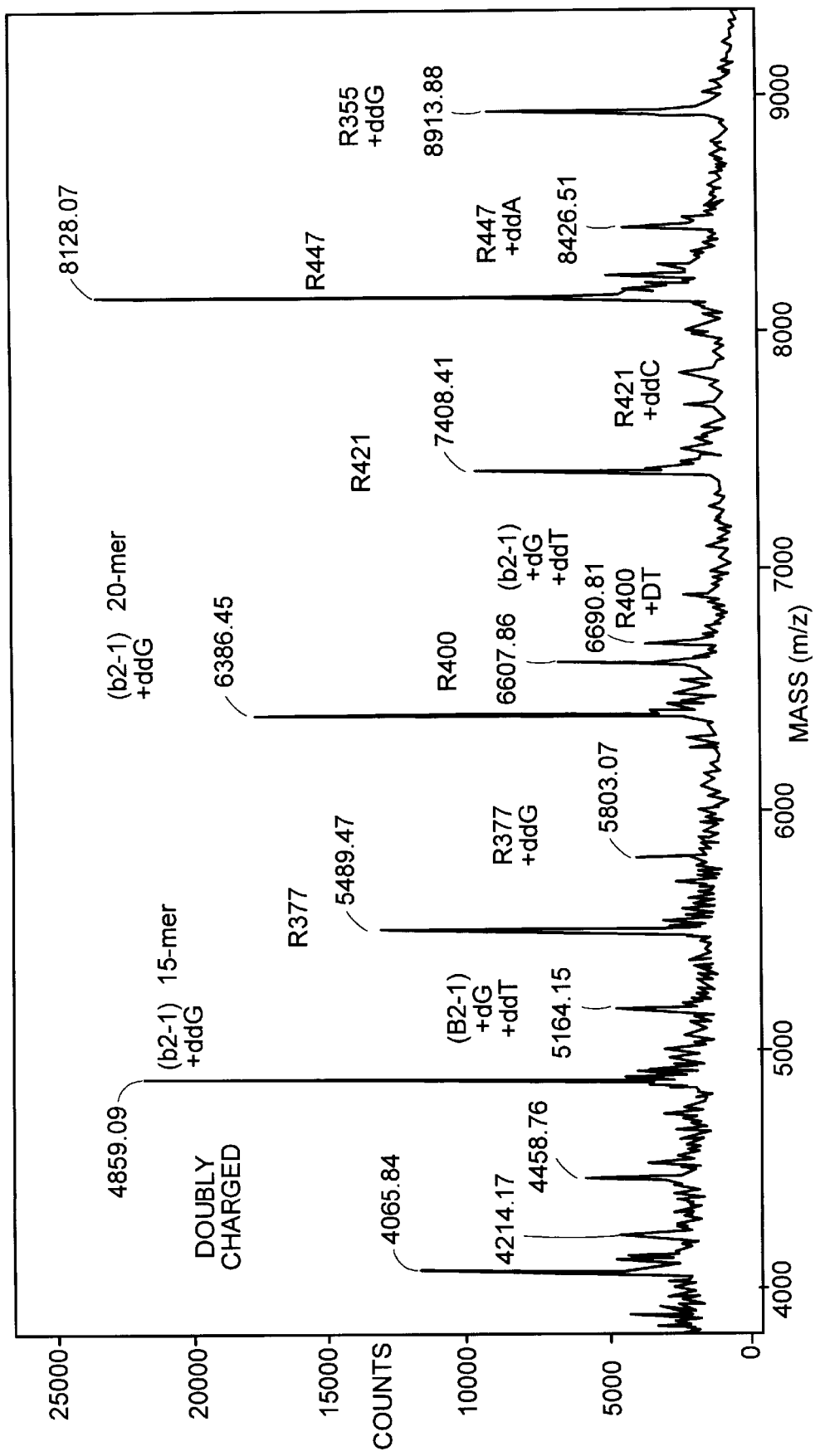
FIG. 6f is a mass spectrum of the results of the multiplex assay performed in the presence of the seven primers whose mass spectrum is shown in FIG. 6f.

In FIG. 6e and 6f, the experiment depicts seven primers designed to examine five loci on the breast cancer susceptibility gene BRCA1 (R355, R377, R400, R421, R447) and one locus on a 60 base synthetic sequence of the lacz gene (b2-1 with a 15-mer and a 20-mer). Two primers hybridizing to the same site (b2-1) but differing in length by five bases were included to determine the effect of the primers' core length on their ability to hybridize with their target site and therefore their ability to undergo nucleotide base extension. All seven primers, shown in FIG. 6e, were extended by the expected nucleotide base. Three of the primers were quantitatively extended within twenty five thermal cycles. In FIG. 6f, all fourteen peaks of the seven primers and the seven extended primers were resolved, but three primers (both b2-1 and R355), were quantitatively extended, while two primers, R400 and R421, produced significantly lower amounts of extended primers than the other primers. Note that both primers b2-1 gave also two extended primers each: the expected nucleotide base ddG and a two-base extension, dGddT, matching to the sequence of the lacz gene downstream of the binding site of the primers b2-1.

Figure 7:
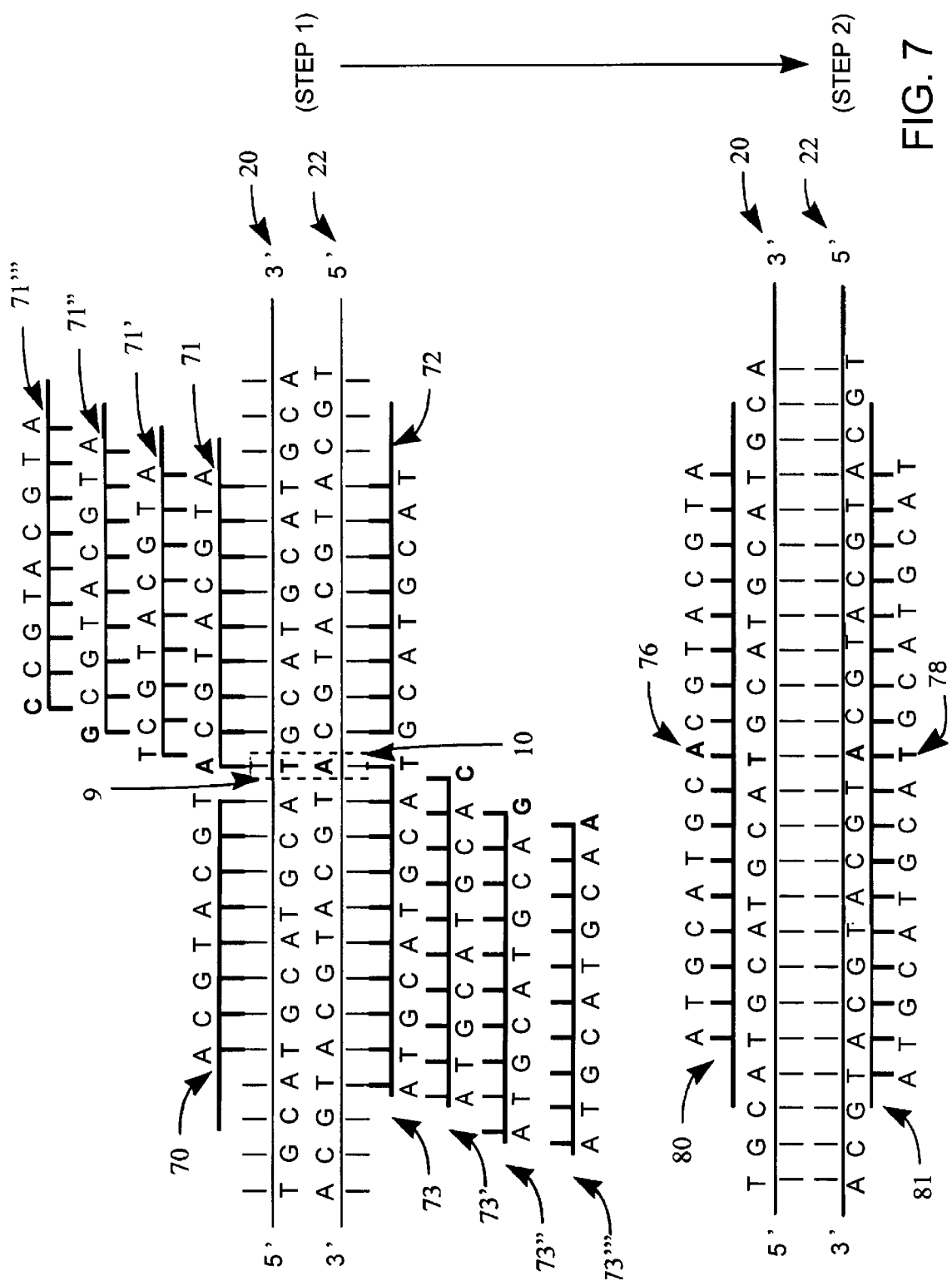
FIG. 7 is a highly schematic diagram of an embodiment of the method for identifying a single putative point mutation in a double stranded DNA using ligase.

In another embodiment, the present invention relates to a method for the identification of single nucleotide polymorphism using ligase chain reaction assay (LCR) on either a single stranded or a double stranded DNA. Referring to FIG. 7, a set of ten oligonucleotide probes 70, 71, 71', 71", 71'", 72, 73, 73', 73" and 73'" are provided to the two strands of a DNA 20, 22 having a single putative point mutation 9, 10. In the first cycle, the oligonucleotide probes are hybridized at the putative point mutation 9, 10 on each strand of DNA 20, 22 such that probes 70 and 71 together overlap the putative mutation site 9 on DNA strand 20 and probes 72 and 73 together overlap the putative mutation site 10 on DNA strand 22 (Step 1). Each set of probes 70, 71, and 72, 73 on

TABLE 2

SNP Primers for Multiplex Assays

| Targets | Core Length (# of bases) | Mass Tag (# of bases) | Total Length (# of bases) | Mass (amu) | Base Extended |
|---|---|---|---|---|---|
| BRCA1 | | | | | |
| R377 | 18 | 0 | 18 | 5,477.58 | ddG |
| F320 | 20 | 0 | 20 | 5,996.94 | ddT |
| R400 | 18 | 4 | 22 | 6,594.34 | ddT |
| R421 | 18 | 8 | 24 | 7,393.64 | ddC |
| R480 | 25 | 0 | 25 | 7,696.04 | ddA |
| R447 | 18 | 8 | 26 | 8,112.34 | ddA |
| R355 | 18 | 10 | 28 | 8,599.61 | ddG |
| lacz | | | | | |
| b2-1 | 15 | 0 | 15 | 4,534.97 | ddG |
| b2-1 | 20 | 0 | 20 | 6,059.95 | ddG |

TABLE 2-continued

SNP Primers for Multiplex Assays

| Targets | SEQ ID nos | Nucleotide Sequence |
|---|---|---|
| BRCA1 | | |
| R377 | SEQ ID no:3 | 5'-TGCTTTGTTC TGGATTTC-3' |
| F320 | SEQ ID no:4 | 5'-AGCCTTCTAA CAGCTACCCT-3' |
| R400 | SEQ ID no:5 | 5'-TTTTACAATA CACACCTTTT TC-3' |
| R421 | SEQ ID no:6 | 5'-TTTTTTTAAG ATATCAGTGT TTGG-3' |
| R480 | SEQ ID no:7 | 5'-CATAAAATGT TGGAGCTAGG TCCTT-3' |
| R447 | SEQ ID no:8 | 5'-TTTTTTTTAT AAAGGGGAAG GAAAGA-3' |
| R355 | SEQ ID no:9 | 5'-TTTTTTTTTT GTCCTCAAGG GCAGAAGA-3' |
| lacz | | |
| b2-1 | SEQ ID no:10 | 5'-GTTTGCCCGC CAGTT-3' |
| b2-1 | SEQ ID no:2 | 5'-CGACTGTTTG CCCGCCAGTT-3' | each DNA strand 20, 22 is then ligated (Step 2) using a ligase and appropriate buffer. In the successive cycles, the ligated probes 80 and 81 will serve as template along with DNA strands 20 and 22 to ligate the probes 70, 71, 72 and 73 resulting in an amplification of the genetic information contained in the segment of DNA 20,22 expressed in the ligated probes 80 and 81. The resulting two ligated oligonucleotide probes 80, 81 are analyzed by mass spectrometry. The ligation step will produce ligated probes 80 and 81 only if the probes 71 and 73 which match the putative point mutation 9, 10 are hybridized to their respective DNA strand. If any of the probes which are only partially hybridized to the DNA in the region of the putative mutation, such as probes 71', 71", 71'", 73', 73" and 73'", then the ligase will not produce a ligated probe. Therefore, the identity of the bases 76 and 78 of the ligated probes 80 or 81 matching the putative point mutation 9, 10 is deduced by measuring their mass and comparing it with the sum of the masses of 70 and 71, 70 and 71', 70 and 71" and 70 and 71'" for ligated probe 80 and the sum of the masses of 72 and 73, 72 and 73', 72 and 73" and 72 and 73'" for ligated probe 81. Once the identity of the bases 76, 78 in the ligated probes 80, 81 is determined, the identity of the bases at the putative point mutation 9, 10 is deduced according to the rules of Watson-Crick base pairing. Note that the information provided by ligated probe 81 is redundant with the information provided by the ligated probe 80 which allows one to deduce the identity of the base at the putative mutation site on the strand of DNA 20. The identity of the base on the second strand 22 can be deduced from the identity of the base on the strand 22 also according to the rules of Watson-Crick base pairing. This redundancy provides for greater reliability in the determination of the assay by providing a second set of data to analyze.

When using a single stranded DNA 20 with LCR, the first cycle will produce only one ligated probe 80 from probes 70 and 71 having a complementary sequence. Then, in the successive cycles, ligated probe 80 and single strand 20, both will serve as a template for the ligation of probes 70, 71, 72 and 73 to produce ligated probes 80 and 81. The subsequent cycles will operate in an amplification of the genetic information as if a double stranded DNA was used initially by producing large amounts of both ligated probes 80 and 81.

In one embodiment, a mass tag is added to one of the probes, for example, to form a tagged probe (not shown). The mass tag may be added to either the 3' end or the 5' end of a probe so long as it is added on the end that does not participate in the ligation between two probes. The number of bases in the resulting ligated probe (not shown) is now increased by the number of bases added in the tag of primer. This mass tagging increases the difference in masses of ligated probes and thus allow a greater resolution in the results of a ligation assay where the masses of ligated probes otherwise would be too close to permit a good resolution of their respective peak by mass spectrometry. This mass tagging may also be used to facilitate the interpretation of the assay experiment by differentiating between primers 71, 71', 71" and 71'" or between primers 73, 73', 73" and 73'".

Figure 8:
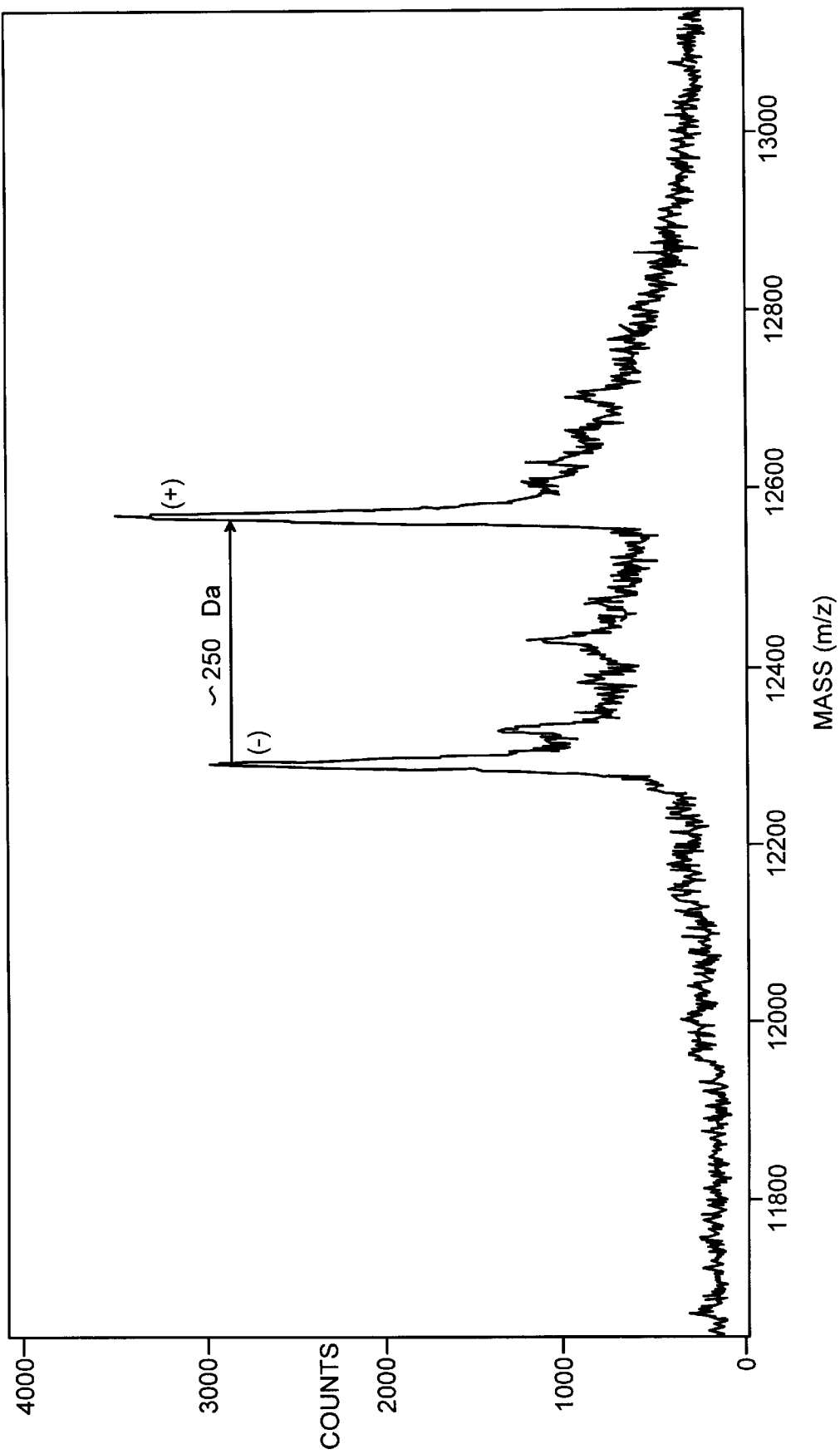
FIG. 8 is a mass spectrum of the results of a ligase assay using an oligonucleotide probe with a mass tag.

Referring to FIG. 8, the results of a single nucleotide (SNP) assay using ligase reaction on a homozygous DNA sample analyzed by mass spectrometry is shown. For this experiment, the target DNA had the following nucleotide sequence:

5'-CTGAATTACA TTCCCAACCG CGTGGCACAA CAA<u>C</u>TGGCGG GCAAACAGTC GTTGCTGATT-3' (SEQ ID NO:1)

wherein <u>C</u> is the point mutation. Two constant probes and eight variable probes were prepared. The sequences of the probes (shown in Table 3) were designed such that a nineteen-base probe with a twenty one-base probe were ligated to form a forty-base ligated oligonucleotide probe and a twenty-base probe with a twenty one-base probe were ligated to form a forty one-base ligated probe.

TABLE 3

Probes for Ligase assay

| Probe | Length | Sequence | SEQ ID NOS | Mass (Da) |
|---|---|---|---|---|
| constant | 19 | 5'-TTGTGCCACGCGGTTGGGA-3' | SEQ ID no:11 | 5955.808 |
| variable | 21 | 5'-CGACTGTTTGCCCGCCAGTTn-3' | SEQ ID no:12 | $6,059.931 + m_x^{(2)}$ |
| variable | 21 | 5'-TTCCCAACCGCGTGGCACAAn-3' | SEQ ID no:13 | $6,046.949 + m_x^{(2)}$ |
| constant | 20 | 5'-AACTGGCGGGCAAACAGTCG-3' | SEQ ID no:14 | 6256.035 |

$^{(1)}$X represents any of A, T, C or G,
$^{(2)}m_x$ represents the mass of nucleotide X.

Figure 9:
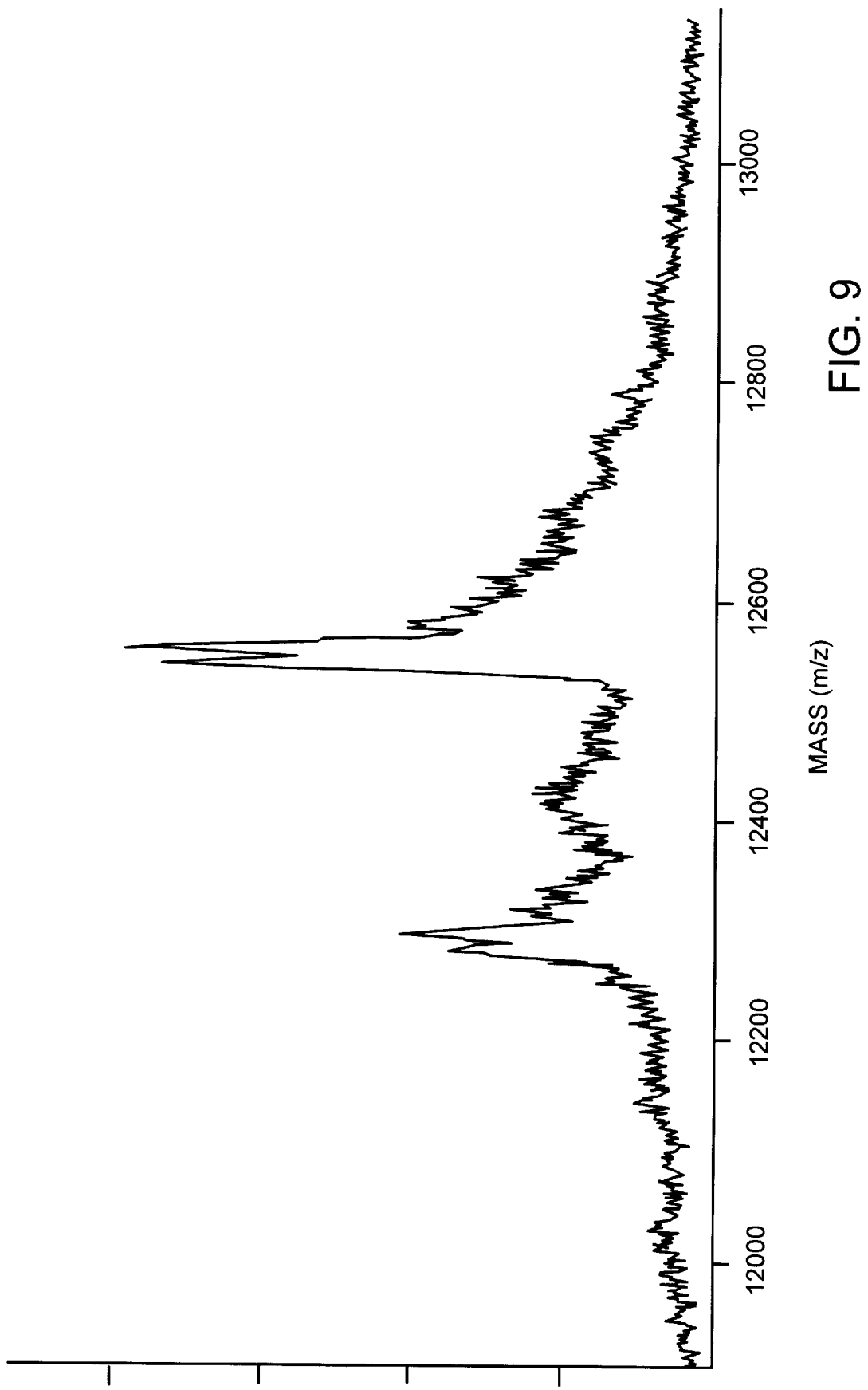
FIG. 9 is a mass spectrum of the results of a ligase assay of heterozygous DNA using multiple oligonucleotide probes with mass tags.

The expected mass for each ligated probes (with <u>G/C</u> at the variable base) is 12,326.93 Da and 12,574.15 Da. As can be seen from FIG. 8, the forty-base and forty one-base ligated probes are easily distinguished from one another with ~248 Da in mass difference. Referring to FIG. 9, the results of a SNP assay using ligase on a heterozygous DNA sample, having both <u>C/T</u> and <u>T/A</u> at the point mutation, analyzed by mass spectrometry is shown. This produced two forty one-base ligated probes with 15.999 Da difference in mass due to G and A, and two forty-base ligated probes with 15.011 Da difference in mass due to C and T.

In another embodiment, the present invention relates to a method for the identification of single nucleotide polymorphism using oligonucleotide ligation assay (OLA) on only one DNA strand 20 having a putative point mutation 9. The method consists of providing a set of five probes 70, 71, 71', 71" and 71 '", one constant 70 and four variable probes 71–71'", wherein the constant probe and only one of the four variable probes hybridize on the DNA 20 such that the two hybridizing probes overlap the putative mutation site and form a perfect match with the base at the putative point mutation 9 of the DNA 20; ligating the two hybridized probes using oligonucleotide ligation assay; identifying the ligated probes by mass spectrometry in a manner similar to the assay using ligation chain reaction with the double stranded DNA.

In yet another embodiment, the present invention includes combinatorial methods for the identification of the nucleotide bases at a putative mutation site that results from either a deletion, an insertion or a substitution of several nucleotide bases by probing more than one nucleotide base at the putative mutation site. Generally, the combinatorial method includes the steps of producing a combination of extended primers of varying length, the combination of extended primers being a ladder sequence defining mixture of short DNA segments where each step of the ladder sequence represents a base at the putative mutation site, and analyzing the combination of extended primers by mass spectrometry (where the mass of each extended primer of specific length defining a step of the ladder sequence). The identity of the sequence at the putative mutation site is deduced by the sequential determination of the mass differences between each step of the ladder sequence starting either from the longest extended primer and proceeding to the initial primer used in the assay or starting from the initial primer and proceeding to the longest extended primer.

Figure 10:
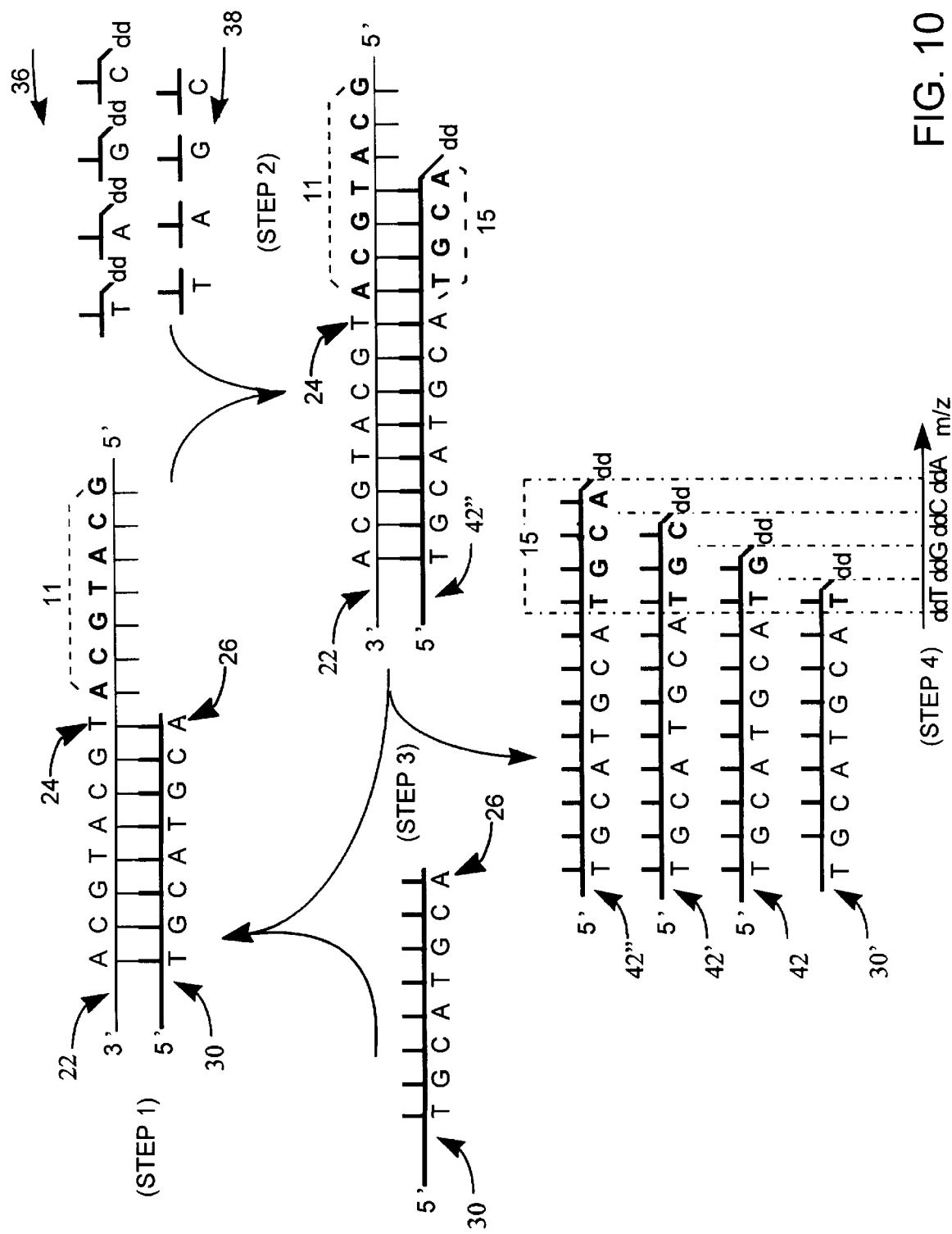
FIG. 10 is a highly schematic diagram of an embodiment of a combinatorial assay used to determine the presence of more than one nucleotide mutation at a putative mutation site.

In more detail and referring to FIG. 10, one embodiment of the combinatorial methods consists of first hybridizing a primer 30 having a sequence complementary to a target DNA segment 22 having a putative mutation site 11 (Step 1). The 3'-end of the primer 30 is positioned adjacent the putative mutation site 11. Next, primer 30 is extended by adding a multiplicity of nucleotide bases 36, 38 on primer 30 (Step 2). For this, each of the possible complementary bases in form of deoxynucleotides 38 and dideoxynucleotides 36, is added to the mixture along with a DNA polymerase and appropriate buffer solution (not shown). Extended primer 30', 42, 42' or 42" is then melted from DNA 22 (Step 3), and DNA 22 is then recycled with excess primer 30 to step 1. At each thermal cycle (Steps 1, 2 and 3), the polymerase extends the primer 30 with the available nucleoside bases 38 and 36 by matching the added bases to the bases of the putative mutation site 11, the DNA 22 serving as a template, until the polymerase either incorporates in the growing primer a stopping base (dideoxynucleotide 36); or the polymerase runs out of available nucleotide bases 38. Thus, by providing a mixture of all the nucleotide bases 36 and 38, the process will generate at each thermal cycle an extended primer 42 of random length. By repeating the thermal cycle a number of times, the process generates a combination of extended primers 30', 42, 42' and 42" of varying length where the sequence of the extended portion 15 of the extended primers is made of deoxynucleotide bases plus the terminal dideoxynucleotide base, all of which match the sequence of the putative mutation site 11 of DNA 22.

Preferably, a thermostable DNA polymerase is used, however, any DNA polymerase can be used provided that, if amplification is required, additional amount of polymerase is added before each thermal cycle. A thermal cycle includes a hybridizing step conducted preferably at 37 ° C. for 60 seconds; a primer extension step; and a denaturing step where the DNA sample is heated to a temperature preferably 95 ° C. for 10 seconds sufficient to melt any DNA/DNA (20,22) helix, any DNA/primer hybrid (22, 30) or any DNA/extended primer (22, 42) duplexes,. The ratio of dideoxynucleotides bases 36 to deoxynucleotide bases 38 (ddNTP:dNTP) for each base may be varied from 1,000:1 to 0.025:1. The preferred range is from about 2:1 to 0.05:1 when thermosequenase is used.

The combination of extended primers 30', 42, 42' and 42" creates a ladder sequence defining mixture wherein each extended primer 30', 42, 42' and 42" represents a step of the ladder sequence. Each extended primer 30', 42, 42' and 42" is terminated by one of the four is dideoxynucleotide bases 36. The mass difference between each step of the ladder sequence therefore corresponds to the mass of one of the four dideoxynucleotide bases 36. The identity of the sequence at the polymorphic site is then determined by measuring the difference in mass between two successive steps of the ladder sequence, correlating the mass to one of the four dideoxynucleotide bases and repeating this for each step of the ladder sequence (Step 4). Once the added sequence 15 on the extended primers is identified, the identity of the sequence at the putative mutation site 11 is deduced by following the rules of Watson-Crick base pairing.

Figure 11:
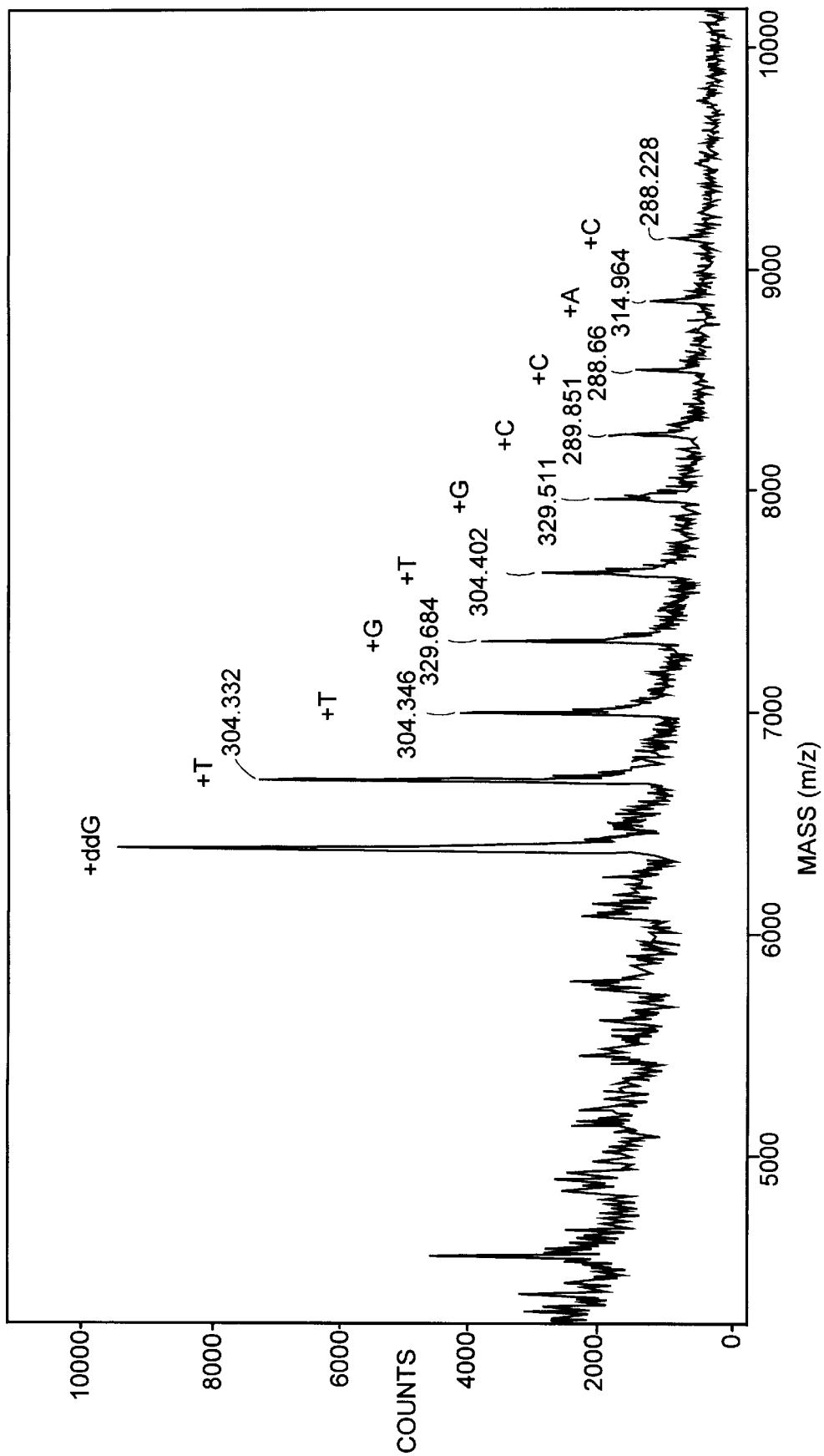
FIG. 11 is a mass spectrum of the results of the combinatorial assay using a polymerase.

Referring to FIG. 11, the results of a combinatorial assay conducted on an oligonucleotide target sequence: 5'-CTGAATTACA TTCCCAACCG C GTGGCACAA CAACTGGCGG GCAAACAGTC GTTGCTGATT-3'(SEQ ID NO:1) where GTGGCACAAC (portion of SEQ ID NO:1) represents the putative mutation site 11. The twenty-base long sequence: 3'-TTGACCGCCC GTTTGTCAGC-5'(SEQ ID NO:2) is used as the primer.

The thermal cycles were conducted on 0.4 $\mu$M of oligonucleotide target sequence in presence of 2 $\mu$M of primer 30, 20 $\mu$M of each triphosphate base (dideoxy and deoxy combined), with a ratio ddNTP:dNTP of 0.1, and 30 units/mL of a Taq DNA polymerase modified at position 667, Thermo Sequenase™, in 25 mM ammonium acetate at pH 9.3 and 2mM magnesium chloride buffer solution. The reaction mixture was thermally cycled at 95° C. for 10 sec., 37° C. for 30 sec. and 72° C. for 60 sec. for 20 cycles in a Perkin Elmer 9600 DNA Thermal Cycler. An amount of 10 $\mu$L of the reaction mixture was then sampled out and applied through a pipette tip packed with a few microliters of POROS™ R1, washed with a 100 mM triethylammonium acetate solution and eluted in about 2 $\mu$L of acetonitrile:water (80:20) solution. The resulting solution was then analyzed by MALDI-TOF mass spectrometry. As seen in FIG. 11, all of the initial primer 30 was extended within the twenty cycles and no peak corresponding to the initial primer 30 is observed in the mass spectrum. The mass spectrum displays the mass of ten extended primers from primer with twenty one bases to primer with thirty bases. The sequence of the added portion 15 is deduced by measuring the mass difference between each step of the ladder sequence and is shown to be 5'-GTTGTGCCAC-3'SEQ ID NO:1. Thus, the sequence of the putative mutation site 11 is deduced as being the complementary sequence: 3'-CAACACGGTG-5'(portion of SEQ ID NO:1).

Figure 12:
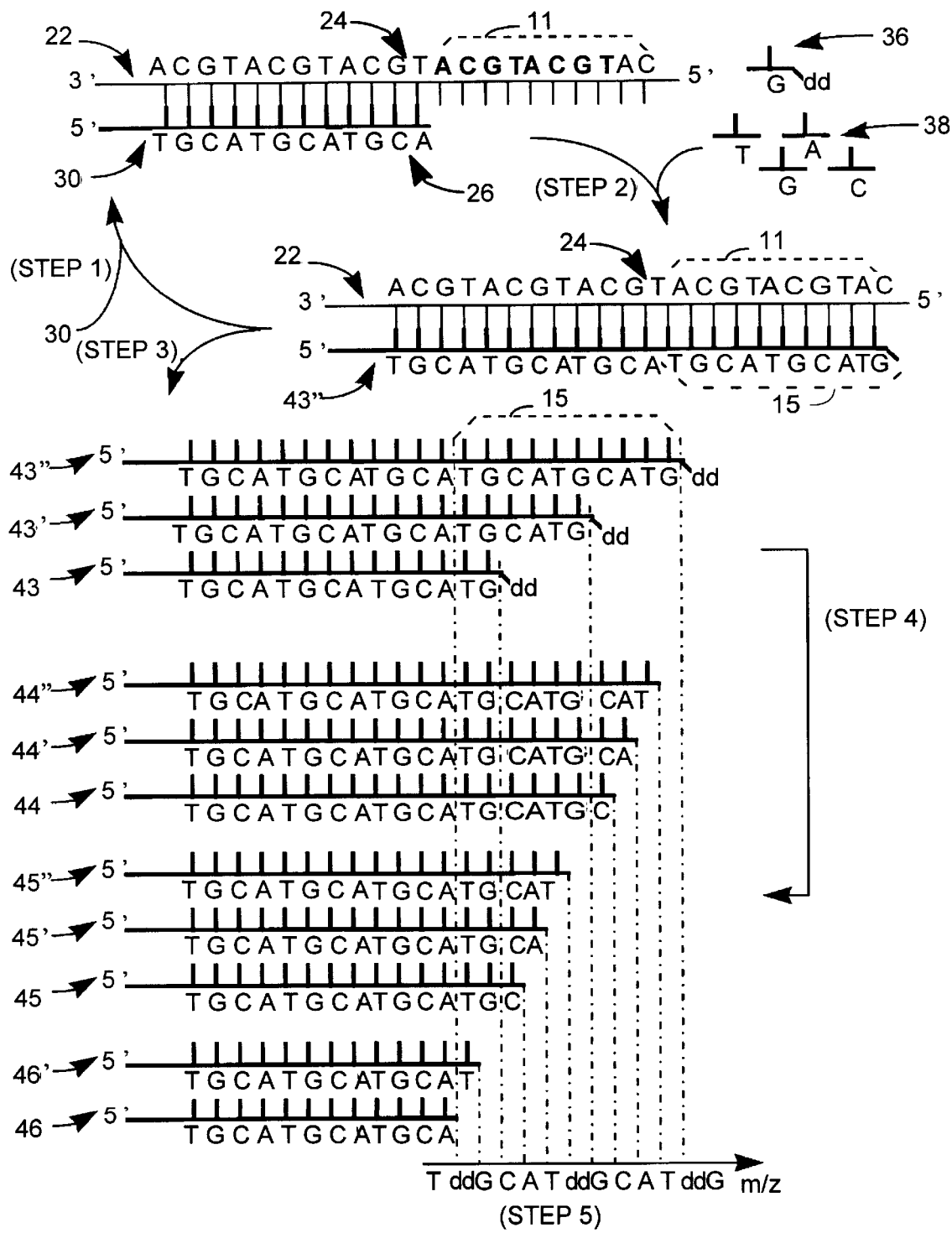
FIG. 12 is a highly schematic diagram of a combinatorial assay used to determine the presence of more than one nucleotide mutation at a putative mutation site followed by digestion by an exonuclease.

In another embodiment, and referring to FIG. 12, the combinatorial method includes hybridizing a primer 30 having a sequence complementary to a target DNA 22 segment having a putative mutation site 11 (Step 1). The 3'end of the primer 30 is adjacent putative mutation site 11. Primer 30 is extended (Step 2) by adding a full set of deoxynucleotide bases 38 with only one of the four dideoxynucleotide bases 36, ddG for example, along with a DNA polymerase and appropriate buffer solution (note shown). The mixture is subjected to the thermal cycle to amplify primer 30 into measurable amounts of extended primers 43, 43'and 43". Again, the last base of each extended primer is the dideoxynucleotide base 36. Since the mass difference between each extended primers 43, 43' and 43" is most likely going to be greater than the mass of one dideoxynucleotide base 36, no sequencing data may be extracted at this stage of the process. The mixture of extended primers 43, 43' and 43" is then subjected to digestion by an exonuclease (Step 4) to create a ladder sequence defining mixture of extended primers of varying length comprising extended primers 43, 43' and 43" and newly formed digested primers 44, 44', 44", 45, 45', 45", 46 and 46'. The addition of a base 36 is to control the length of the extended primers, otherwise the primer 30 would be extended for a long and undefined length and its molar concentration would be too low be detected by mass spectrometry. By limiting the primer extension to a relative short length, a high molar concentration of the extended primers may be attained. Also, by producing a controlled distribution in length of the extended primers before the digestion step, a controlled distribution in length of the digested primers may be attained with detectable molar concentrations. The combination of extended primers and digested primers defines a ladder sequence where the mass difference between extended primer 43 and first digested primer 44, for example, is the mass of dideoxynucleotide base 36 and the mass difference between each successive step of the ladder sequence formed by digested primers 44 and 44' or 44' and 44", for example, is the mass of one of the four deoxynucleotide base 38. To facilitate the reading of the mass spectrum resulting from the digestion, it is preferable to record a mass spectrum of the mixture of extended primers 43, 43' and 43" before effecting the digestion to help locate their peaks in the mass spectrum resulting from the digestion. Once every step of the ladder sequence has been attributed to either a base 36 or 38 (Step 5), the sequence of the putative mutation site is deduced by following the rules of Watson-Crick base pairing. This method is particularly well suited when the number of bases to be determined at the putative mutation site 11 is greater than ten.

The digestion of the mixture of extended primers 43, 43' and 43" may be carried with any known exonuclease such as phosphodiesterase type I, exonuclease I, exonuclease III, exonuclease V, exonuclease VII, and DNA polymerase III.

Figure 13:
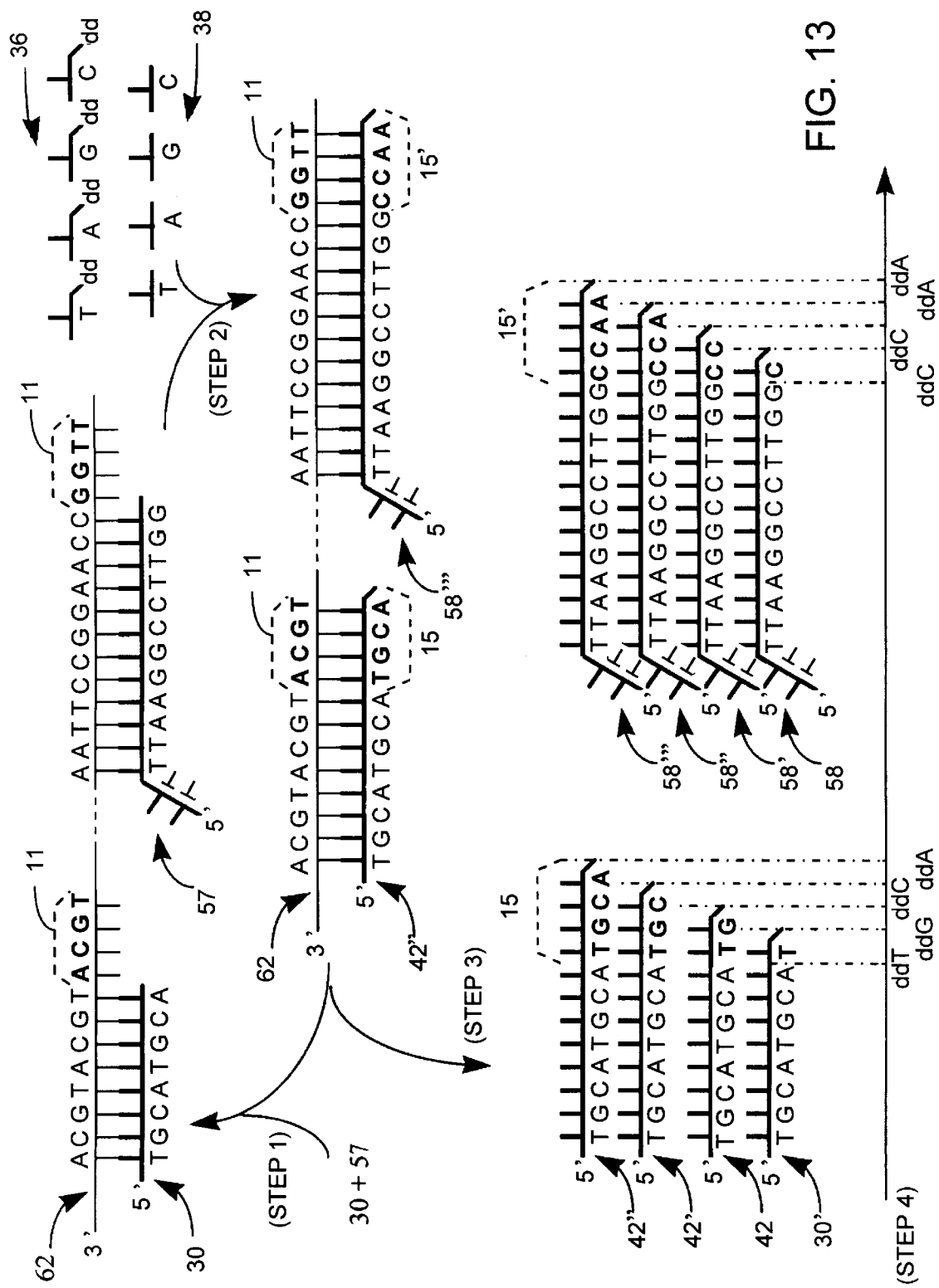
FIG. 13 is a highly schematic diagram of a multiplex combinatorial assay on a DNA having multiple putative mutation sites of more than one nucleotide base mutation.

In still yet another embodiment, the present invention provides a multiplex combinatorial method for the identification of multiple putative mutation sites that result from a deletion, an insertion or a multiple substitution of a nucleotide base. In referring to FIG. 13, the methods include hybridizing a multiplicity m of primers 30 and 58, each having a sequence complementary and to a putative mutation site 11 and 11 ' respectively, of a DNA 62 having more than one putative mutation site (Step 1). Next the method extends the multiplicity m of primers in the presence of a multiplicity of nucleotide bases 36 and 38 with a DNA polymerase and appropriate buffer solution (not shown) such that each primer is extended by more than one nucleotide base (Step 2). The multiplicity of extended primers 30' and 58 is melted from DNA 62 (Step 3) and DNA 62 is recycled (Step 1) to hybridize with excess of primers 30 and 57. At each cycle, the polymerase extends the multiplicity of primers 30 and 57 with the available nucleotide bases 36 and 38 by matching the added bases at the polymorphic sites 11 and 11', the DNA 62 serving as a template, producing a multiplicity of extended primers 53' 42, 42", 58, 58', 58" and 58'". Finally, the combination of extended primers is identified by mass spectrometry (Step 4). The combination of extended primers defines a series of ladder sequences, each ladder sequence being an imprint of each putative mutation site 11 and 11'. The sequence of each putative mutation site is then determined by subtracting the masses between two adjacent steps of each ladder sequence and attributing the mass difference to anucleotide base. The base at the putative mutation site is then deduced according to the rules of Watson-Crick base pairing. This is repeated for every step of a ladder sequence.

In still another embodiment, the multiplex combinatorial method includes the combination of primer extension and digestion. First, a multiplicity m of primers, each having a sequence complementary and adjacent a putative mutation site of a DNA from a sample having more than one putative mutation site is hybridized to the DNA. Next, the multiplicity m of primers is amplified in the presence of a multiplicity of deoxynucleotide bases and at least one dideoxynucleotide base with a polymerase and appropriate buffer solution so that each primer is extended by more than one nucleotide base. Third, the multiplicity of extended primers is subjected to a digestion using an exonuclease. Finally, the combination of extended and digested primers is analyzed by mass spectrometry. The sequence of each putative mutation site is then determined as described earlier. To attain a good resolution of the mass spectrum obtained from the combination of extended primers, it is preferred to use a multiplicity m of primers wherein (m-1) primers have a mass tag on their 5' end.

In yet other embodiments, the methods of present the invention relates to the identification of nucleotide polymorphisms in RNA target sequences. Any of the methods described above can be applied to determine polymorphism in an RNA by substituting an RNA target in place of a DNA target and reverse transcriptase in place of DNA polymerase. In a preferred embodiment, thermal cycles are performed using a thermostable reverse transcriptase, such as thermophilus (rTth) DNA polymerase for example.

Figure 14:
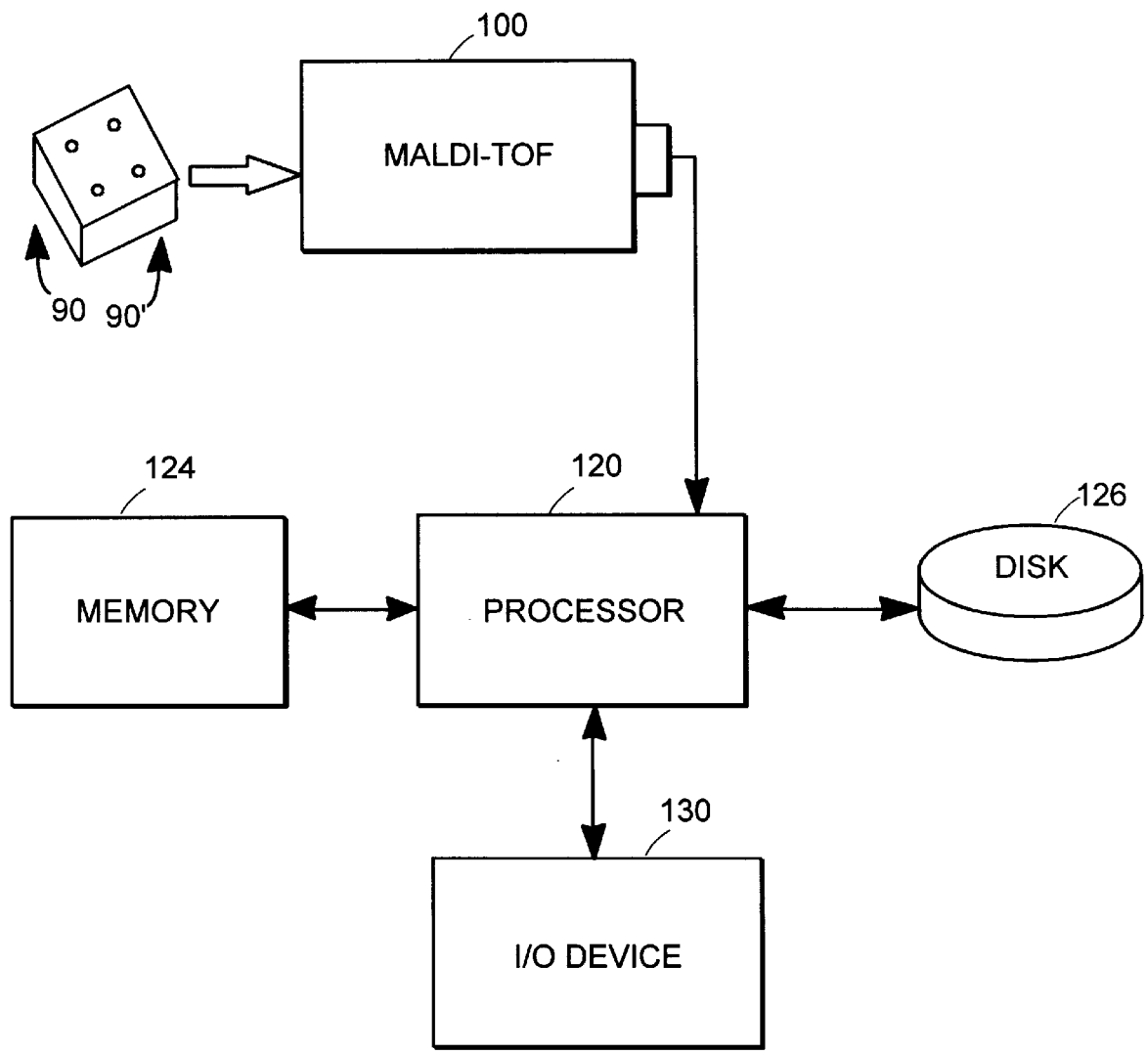
FIG. 14 is a highly schematic diagram of an embodiment of an instrument used to practice the invention.

A highly schematic diagram of an instrument used to perform the various methods of the invention is depicted in FIG. 14. Each of the primers to be used are added separately to a sample plate 90 which includes a series of sample locations; one for each primer. The sample plate 90 is placed in a MALDI-TOF spectrometer 100 which determines the mass of each of the individual primers used in the sequencing. Next the hybridized modified primer and target polynucleotide is added to a sample plate 90' and this sample plate 90' is placed in the MALDI-TOF spectrometer 100. The mass of the modified primer and the mass of the target polynucleotide are then determined; the hybridization being destroyed by the laser light during the desorption ionization process which occurs within the MALDI-TOF 100.

A processor 120 which may be a general purpose computer or a specialized processor collects the mass data from the MALDI-TOF 100 and places the data into memory 124 and optionally onto a disk or other off-line storage 126. The processor 120 then determines the mass difference between each primer and its corresponding modified primer. The processor 120 then compares the mass difference for each primer with a table of nucleotide masses stored on disk 126 and read into memory 124. From this tabular comparison of the mass difference of the primer and the modified primer with the nucleotide base masses, the nucleotide additions to the primer is then determined. The results are either displayed to the user 130 or stored on disk 126 for later analysis.

Figure 15:
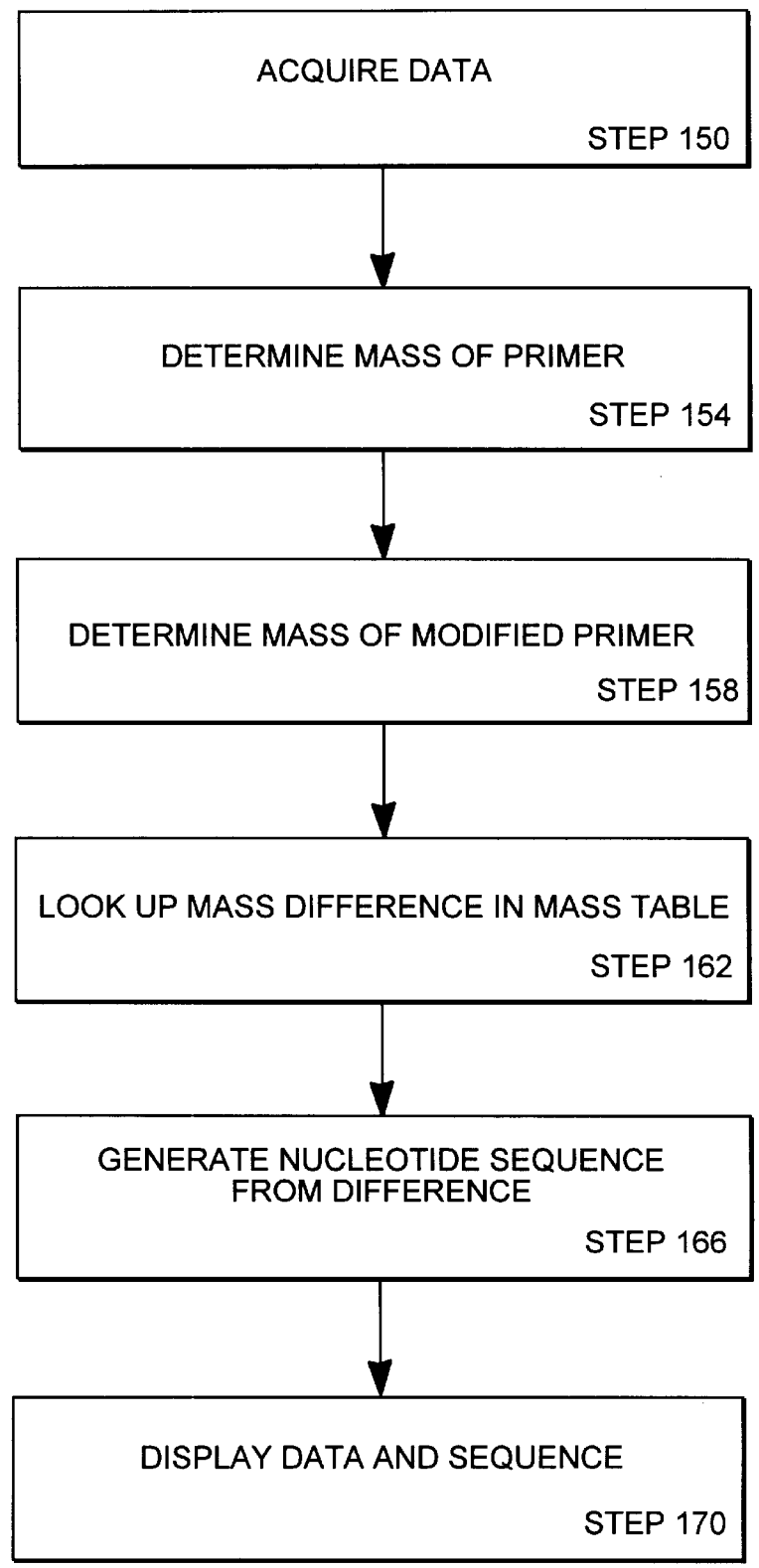
FIG. 15 is a flow diagram of an embodiment of an algorithm used in conjunction with the instrument shown in FIG. 14.

Briefly, and referring to FIG. 15, an embodiment of an algorithm to determine sequence data includes the step of taking the mass data from the MALDI-TOF 100 (Step 150) and from the data determining the mass of each of the primer used (Step 154) and each modified primer formed (Step 158). The table of nucleotide masses located in memory 124 is compared (Step 162) to the mass differences determined in the previous step. By knowing the individual masses of the nucleotides, the nucleotide sequence is generated (Step 166). Once the data and sequence have been determined, the data and/or the sequence are displayed (Step 170) on the user's I/O device such as a terminal 130 or are stored in off line storage 126.

Having described preferred embodiments of the invention, it will now become apparent to one of skilled in the art that other embodiments incorporating the concepts disclosed herein may be used. It is felt, therefore, that these embodiments should not be limited to disclosed embodiments but rather should be limited only by the spirit and scope of the following claims.

What is claimed is:

1. A method for identifying a putative point mutation in a polynucleotide using mass spectrometry, comprising the steps of:
 a. providing a primer having a sequence that hybridizes adjacent said putative point mutation of said single strand of said polynucleotide;
 b. heating said polynucleotide and said primer to a temperature sufficient to melt said polynucleotide; and
 c. cooling said melted polynucleotide and said primer to a temperature sufficient to hybridize said primer to said single strand of said polynucleotide, thereby forming a duplex wherein the 3'-end of said primer is hybridized adjacent the putative point mutation of said single strand of said polynucleotide;
 d. extending the 3'-end of said primer by adding a single dideoxynucleotide base complementary to the putative point mutation of the polynucleotide, wherein said dideoxynucleotide base has a mass range of about 273 to about 313,
 using a polynucleotide thermostable polymerase having substantially the same relative rate of incorporation of dideoxynucleotide bases as deoxynucleotide bases, thereby forming an extended primer; and
 e. analyzing the extended primer using mass spectrometry to determine the identity of the dideoxynucleotide base at the putative point mutation
 wherein steps a–d are repeated a sufficient number of times to permit detection of said extended primer by mass spectrometry.

2. A method for identifying a putative point mutation in a polynucleotide using mass spectrometry, comprising the steps of:
 a. hybridizing a primer comprising a mass tag to a single strand of said polynucleotide having a putative point mutation, the 3'-end of said primer being hybridized adjacent the putative point mutation;
 b. extending the 3'-end of said primer by adding a single dideoxynucleotide base complementary to the putative point mutation of the polynucleotide, wherein said dideoxynucleotide base has a mass range of about 273 to about 313,
  using a polynucleotide thermostable polymerase having substantially the same relative rate of incorporation of dideoxynucleotide bases as deoxynucleotide bases,
  thereby forming an extended primer; and
 c. analyzing the extended primer using mass spectrometry to determine the identity of the dideoxynucleotide base at the putative point mutation,
 wherein steps a and b are repeated a sufficient number of times to permit detection of said extended primer.

3. The method of claim 2, wherein the mass tag is a polythmidylate, $T_n$, on the 5'-end of said primer, wherein n is an integer ranging from 1 to 40.

4. The method of claim 1, wherein said polynucleotide is a DNA and said polynucleotide polymerase is a Taq DNA polymerase modified at position 667.

5. The method of claim 1, wherein said polymerase is provided in a buffer volatile under conditions present in a mass spectrometer.

6. The method of claim 1, wherein step (e) is accomplished using matrix assisted laser desorption ionization time-of-flight (MALDI-TOF) mass spectrometry.

7. A multiplex method for identifying a plurality of putative point mutations in at least one polynucleotide using mass spectrometry, comprising the steps of:

a. providing a plurality of pairs each having a sequence that hybridizes adjacent a respective putative point mutation of said at least one polynucleotide;

b. heating said at least one polynucleotide and said plurality of primers to a temperature sufficient to melt said at least one polynucleotide; and c. cooling said at least one melted polynucleotide and said plurality of primers to a temperature sufficient to hybridize the plurality of primers to said at least one single strand of said at least one polynucleotide, thereby forming a multiplex wherein the 3'-end of each one of said plurality of primers is hybridized adjacent a respective one of said plurality of putative point mutations;

d. extending the 3'-end of said plurality of primers by adding one of a plurality of dideoxynucleotide bases to said plurality of hybridized primers, wherein said dideoxynucleotide base has a mass range of about 273 to about 313, using a polynucleotide thermostable polymerase having substantially the same relative rate of incorporation of dideoxynucleotide bases as deoxynucleotide bases, whereby one of said plurality of said dideoxynucleotide bases complementary to said respective one of said plurality of putative point mutations is added to the respective one of said plurality of hybridized primers, thereby forming a plurality of extended primers each having one added dideoxynucleotide base; and e. analyzing the plurality of extended primers using mass spectrometry to determine the identity of the dideoxycleotide base at each putative point mutation wherein steps a–d are repeated a sufficient number of times to permit detection of said extended primers by mass spectrometry.

8. A multiplex method for identifying a plurality of putative point mutations in at least one polynucleotide using mass spectrometry, comprising the steps of:

a. hybridizing a plurality of primers, each having a 3'-end and a 5'-end, to at least one single strand of said at least one polynucleotide having said plurality of putative point mutations, the 3'-end of each of said plurality of primers being hybridized adjacent a respective one of said plurality of putative point mutations;

b. extending the 3'-end of said plurality of primers by adding one of a plurality of dideoxynucleotide bases to said plurality of hybridized primers, wherein said dideoxynucleotide base has a mass range of about 273 to about 313, using a polynucleotide thermostable polymerase having substantially the same relative rate of incorporation of dideoxynucleotide bases as deoxynucleotide bases, whereby one of said plurality of dideoxynucleotide bases complementary to said respective one of said plurality of putative point mutations is added to the respective one of said plurality of hybridized primers, thereby forming a plurality of extended primers each having one added dideoxynucleotide base; and c. analyzing the plurality of extended primers using mass spectrometry to determine the identity of the dideoxynucleotide base at each putative point mutation wherein steps a and b are repeated a sufficient number of times to permit detection of said extended primers by mass spectrometry and at least one primer comprises a mass tag.

9. The multiplex method of claim 8, wherein said mass tag is a polythymidylate: $T_n$, on the 5'-end of said at least one primer wherein n is an integer ranging from 1 to 40.

10. The multiplex method of claim 7, wherein said at least one polynucleotide is a DNA and said polymerase is a Taq DNA polymerase modified at position 667.

11. The multiplex method of claim 7, wherein said polymerase is provided in a buffer volatile under conditions present in a mass spectrometer.

12. The multiplex method of claim 7, wherein step (e) is accomplished using matrix assisted laser desorption ionization time-of-flight (MALDI-TOF) mass spectrometry.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
( A ) LENGTH: 60 base pairs
( B ) TYPE: nucleic acid
( C ) STRANDEDNESS: single
( D ) TOPOLOGY: linear ( x i ) SEQUENCE DESCRIPTION: SEQ ID NO:1:

CTGAATTACA TTCCCAACCG CGTGGCACAA CAACTGGCGG GCAAACAGTC GTTGCTGATT        60

( 2 ) INFORMATION FOR SEQ ID NO:2:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:2:

CGACTGTTTG CCCGCCAGTT        20

( 2 ) INFORMATION FOR SEQ ID NO:3:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:3:

TGCTTTGTTC TGGATTTC        18

( 2 ) INFORMATION FOR SEQ ID NO:4:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:4:

AGCCTTCTAA CAGCTACCCT        20

( 2 ) INFORMATION FOR SEQ ID NO:5:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( x i ) SEQUENCE DESCRIPTION: SEQ ID NO:5:

TTTTACAATA CACACCTTTT TC        22

( 2 ) INFORMATION FOR SEQ ID NO:6:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( x i ) SEQUENCE DESCRIPTION: SEQ ID NO:6:

TTTTTTTAAG ATATCAGTGT TTGG    24

( 2 ) INFORMATION FOR SEQ ID NO:7:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

CATAAATGT TGGAGCTAGG TCCTT    25

( 2 ) INFORMATION FOR SEQ ID NO:8:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

TTTTTTTAT AAAGGGGAAG GAAAGA    26

( 2 ) INFORMATION FOR SEQ ID NO:9:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

TTTTTTTTT GTCCTCAAGG GCAGAAGA    28

( 2 ) INFORMATION FOR SEQ ID NO:10:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

GTTTGCCCGC CAGTT    15

( 2 ) INFORMATION FOR SEQ ID NO:11:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

TTGTGCCACG CGGTTGGGA    19

( 2 ) INFORMATION FOR SEQ ID NO:12:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

```
CGACTGTTTG CCCGCCAGTT N                                                          21
```

( 2 ) INFORMATION FOR SEQ ID NO:13:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:13:

```
TTCCCAACCG CGTGGCACAA N                                                          21
```

( 2 ) INFORMATION FOR SEQ ID NO:14:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:14:

```
AACTGGCGGG CAAACAGTCG                                                            20
```

( 2 ) INFORMATION FOR SEQ ID NO:15:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:15:

```
GTTGTGCCAC                                                                       10
```